United States Patent
Blomberg

(10) Patent No.: US 7,780,609 B2
(45) Date of Patent: Aug. 24, 2010

(54) TEMPORARY THRESHOLD SHIFT DETECTOR

(76) Inventor: Leslie David Blomberg, 20 Pleasant St., Montpelier, VT (US) 05602

( * ) Notice: Subject to any disclaimer, the term of this patent is extended or adjusted under 35 U.S.C. 154(b) by 0 days.

(21) Appl. No.: 11/823,351

(22) Filed: Jun. 27, 2007

(65) Prior Publication Data

US 2008/0015464 A1  Jan. 17, 2008

Related U.S. Application Data

(60) Provisional application No. 60/816,839, filed on Jun. 27, 2006.

(51) Int. Cl.
  A61B 5/00   (2006.01)
  A61B 5/12   (2006.01)
(52) U.S. Cl. .......... 600/559; 73/585
(58) Field of Classification Search ......... 600/559; 73/585
  See application file for complete search history.

(56) References Cited

U.S. PATENT DOCUMENTS

| | | | |
|---|---|---|---|
| 3,718,763 A * | 2/1973 | Cannon et al. | 73/585 |
| 3,970,785 A | 7/1976 | Meyer | |
| 4,024,499 A * | 5/1977 | Bosscher | 340/146.2 |
| 4,107,465 A * | 8/1978 | Charlebois et al. | 73/585 |
| 4,284,847 A * | 8/1981 | Besserman | 73/585 |
| 4,748,598 A * | 5/1988 | Kopke | 367/13 |
| 5,143,081 A * | 9/1992 | Young et al. | 600/554 |
| 5,928,160 A | 7/1999 | Clark | |
| 6,350,243 B1 | 2/2002 | Johnson | |
| 7,210,353 B2 * | 5/2007 | Braun et al. | 73/585 |
| 7,288,072 B2 * | 10/2007 | Stott et al. | 600/559 |
| 7,370,533 B2 * | 5/2008 | Davis | 73/585 |
| 7,464,595 B2 * | 12/2008 | Davis | 73/585 |
| 2002/0078750 A1 * | 6/2002 | Wright et al. | 73/585 |
| 2003/0070485 A1 * | 4/2003 | Johansen et al. | 73/585 |
| 2004/0074304 A1 * | 4/2004 | Braun et al. | 73/585 |
| 2004/0127812 A1 * | 7/2004 | Micheyl et al. | 600/559 |
| 2005/0085744 A1 * | 4/2005 | Beverina et al. | 600/558 |
| 2005/0192514 A1 * | 9/2005 | Kearby et al. | 600/559 |
| 2006/0058701 A1 * | 3/2006 | Bolles et al. | 600/558 |
| 2006/0153395 A1 * | 7/2006 | van Den Heuvel et al. | 381/60 |
| 2006/0277999 A1 * | 12/2006 | Raviv | 73/585 |
| 2007/0135730 A1 * | 6/2007 | Cromwell et al. | 600/559 |
| 2007/0204694 A1 * | 9/2007 | Davis | 73/585 |
| 2007/0204695 A1 * | 9/2007 | Gross et al. | 73/585 |
| 2007/0276285 A1 * | 11/2007 | Burrows et al. | 600/559 |
| 2008/0167575 A1 * | 7/2008 | Cronin et al. | 600/559 |
| 2008/0194984 A1 * | 8/2008 | Keefe | 600/559 |

* cited by examiner

Primary Examiner—Max Hindenburg
Assistant Examiner—Sean P Dougherty
(74) Attorney, Agent, or Firm—James Marc Leas

(57) ABSTRACT

A method of detecting a change in hearing of a user includes providing a sound generating device for providing both a content audio signal and a hearing test audio signal. The sound generating device is used to provide hearing test audio sounds of different loudnesses around a threshold of hearing of the user. None of these sounds is calibrated to a pre-specified decibel level. A first threshold of hearing is determined at a first time and a second threshold of hearing is determined at a second time. The first threshold of hearing is compared with the second threshold of hearing.

24 Claims, 20 Drawing Sheets

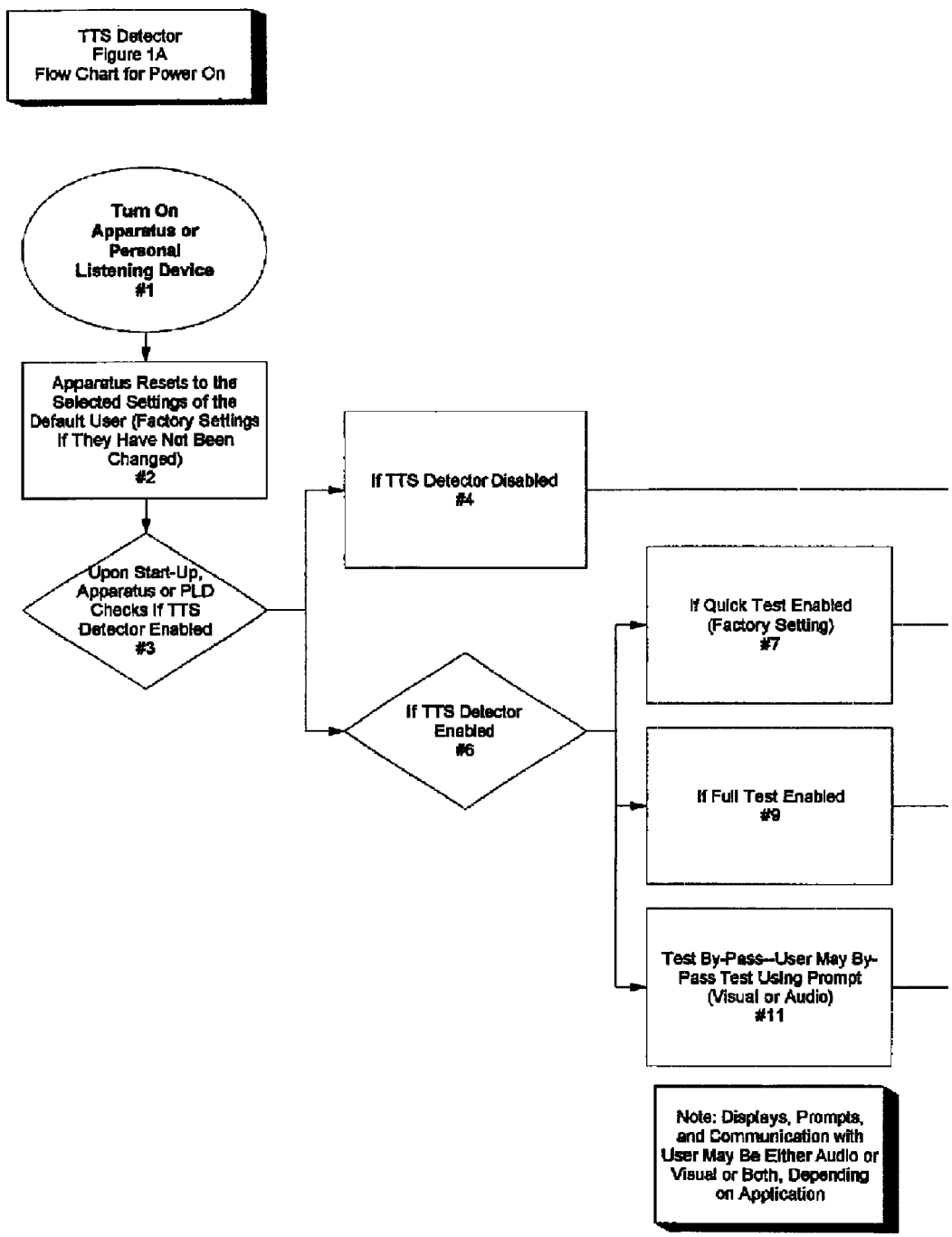

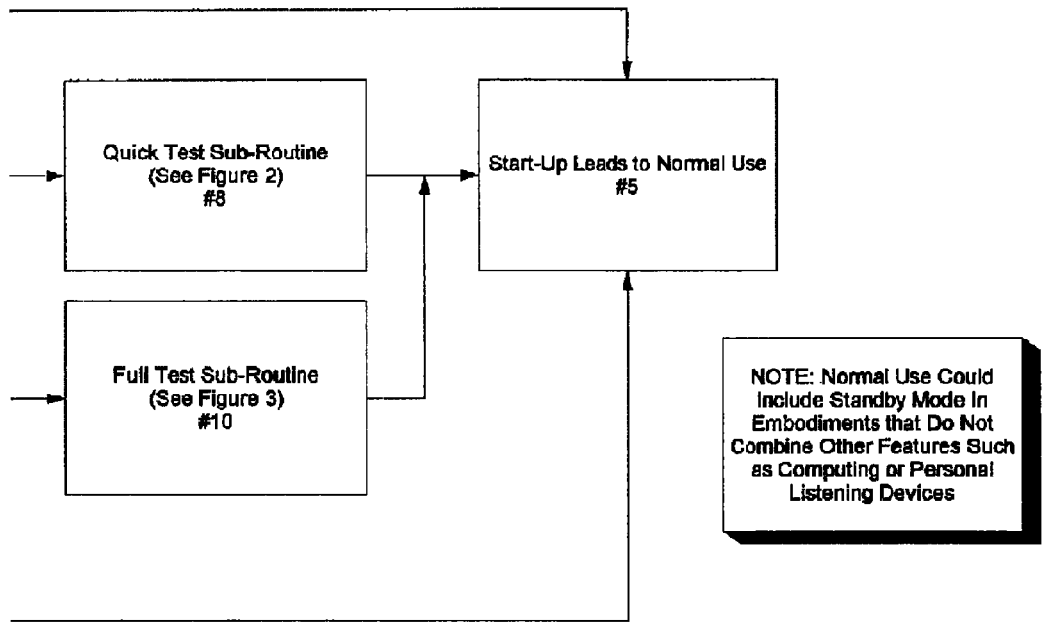

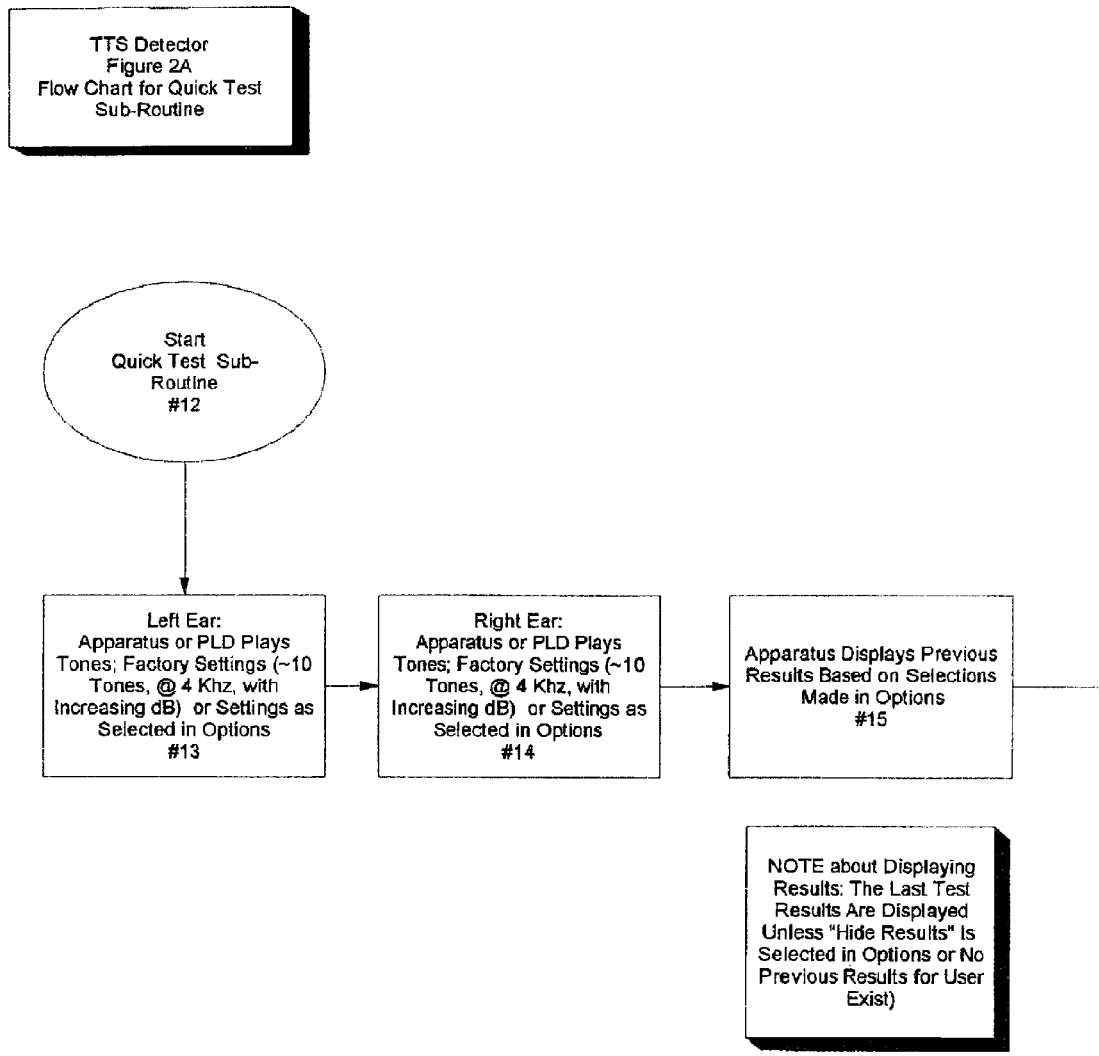

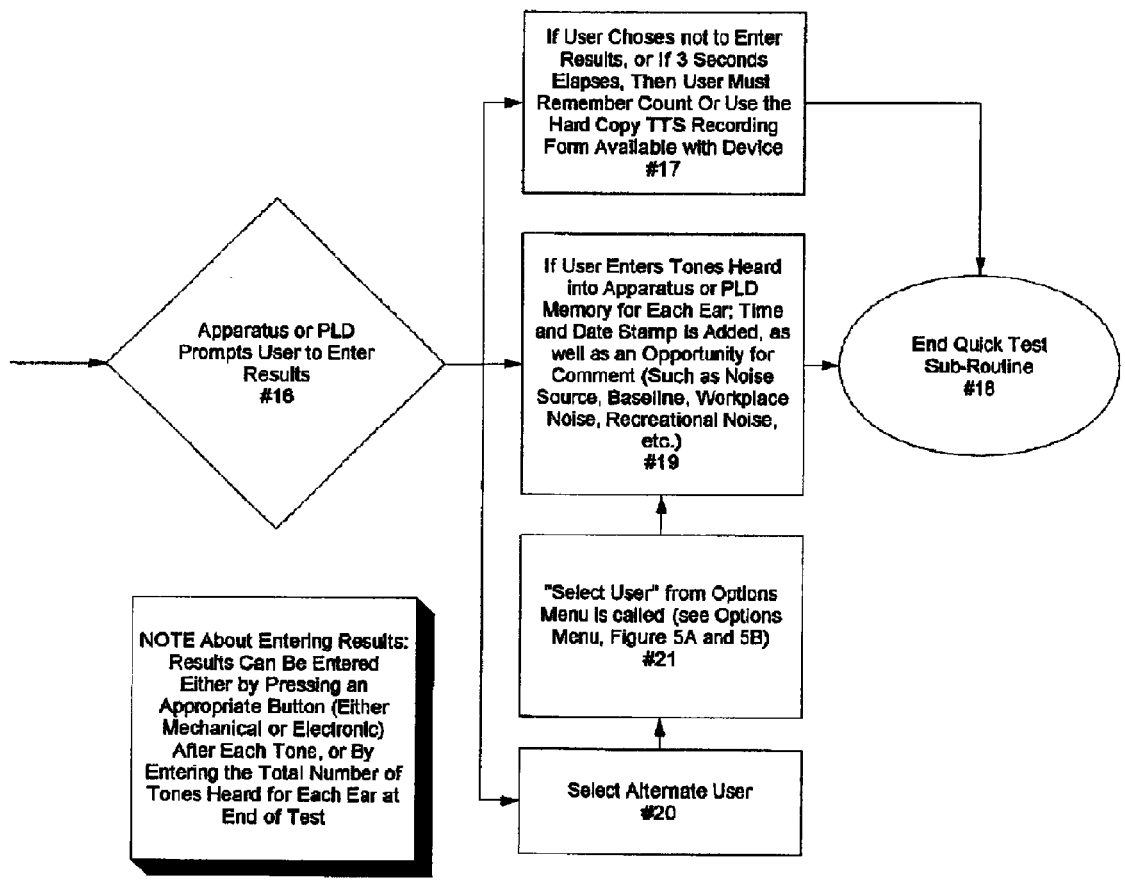

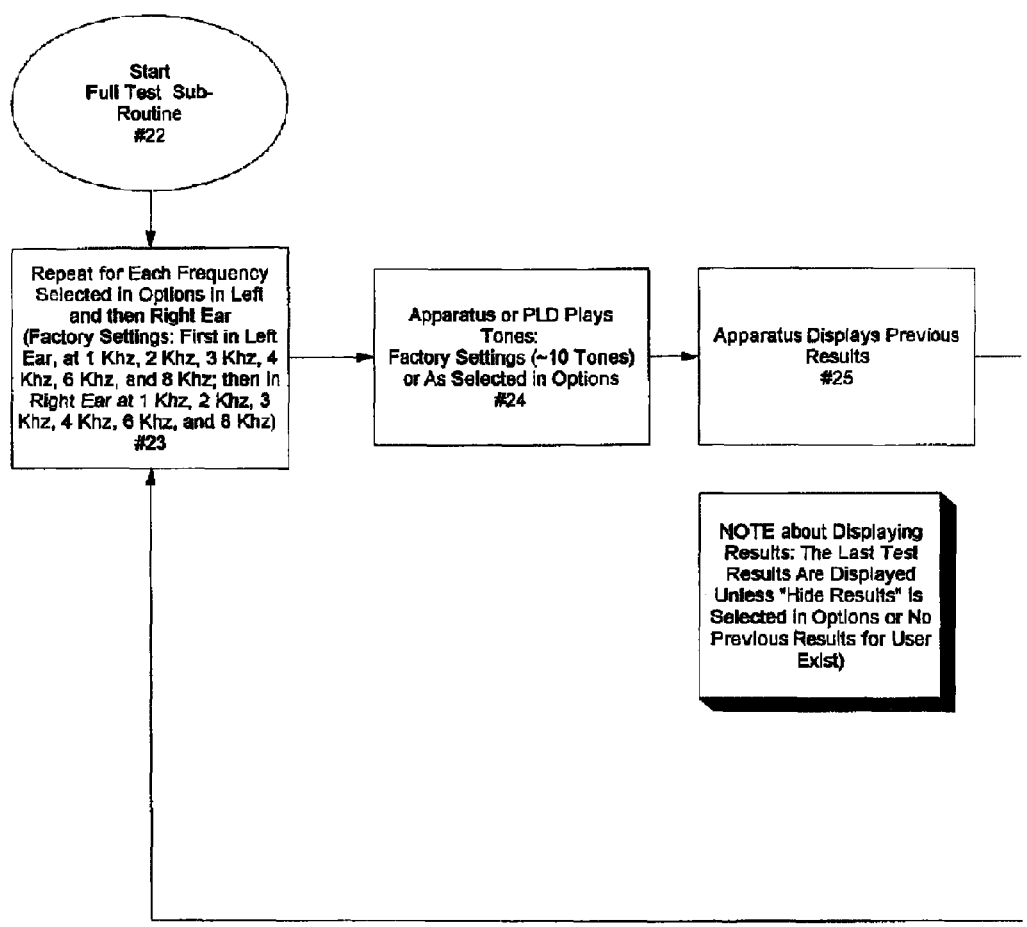

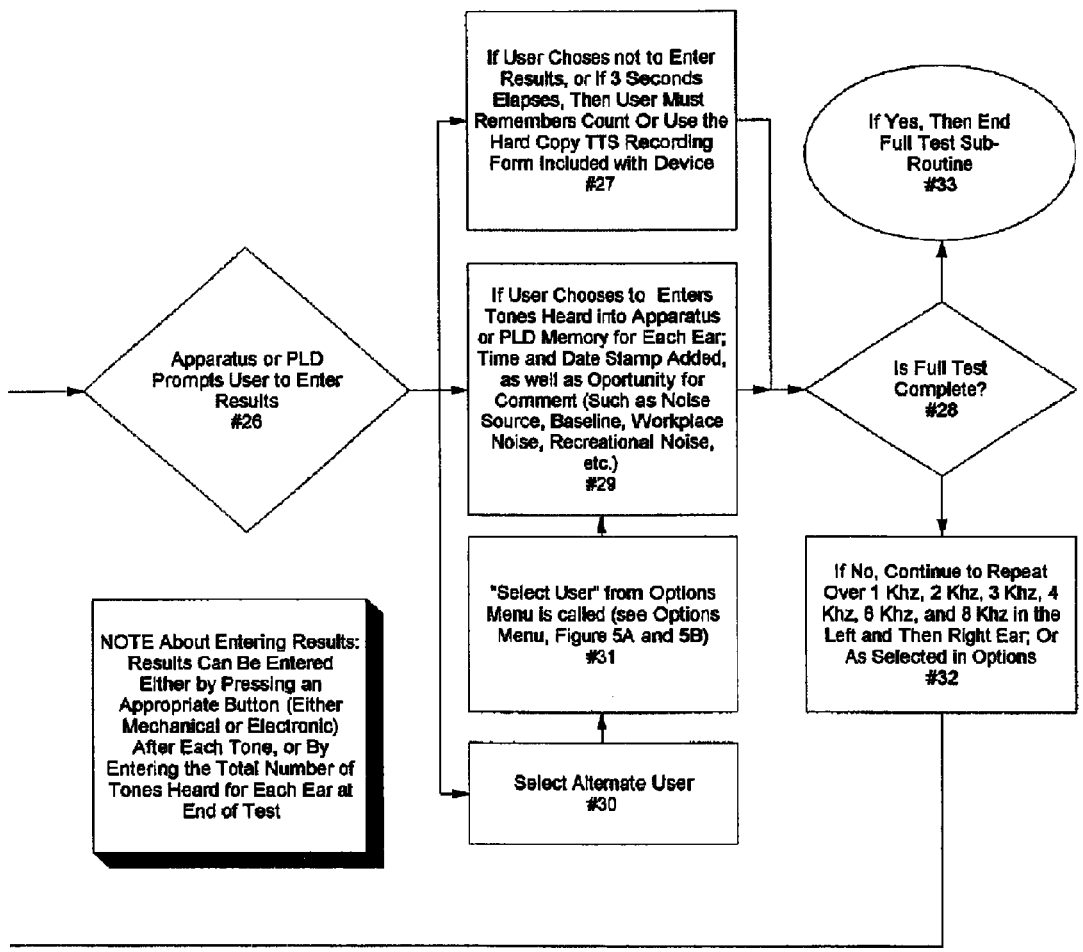

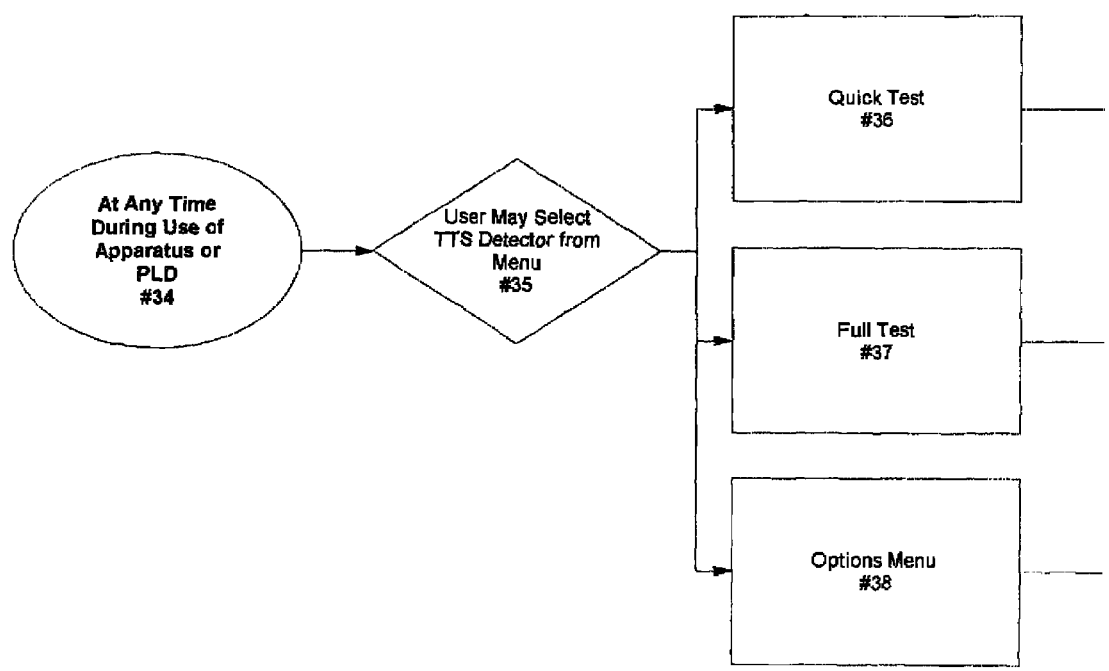

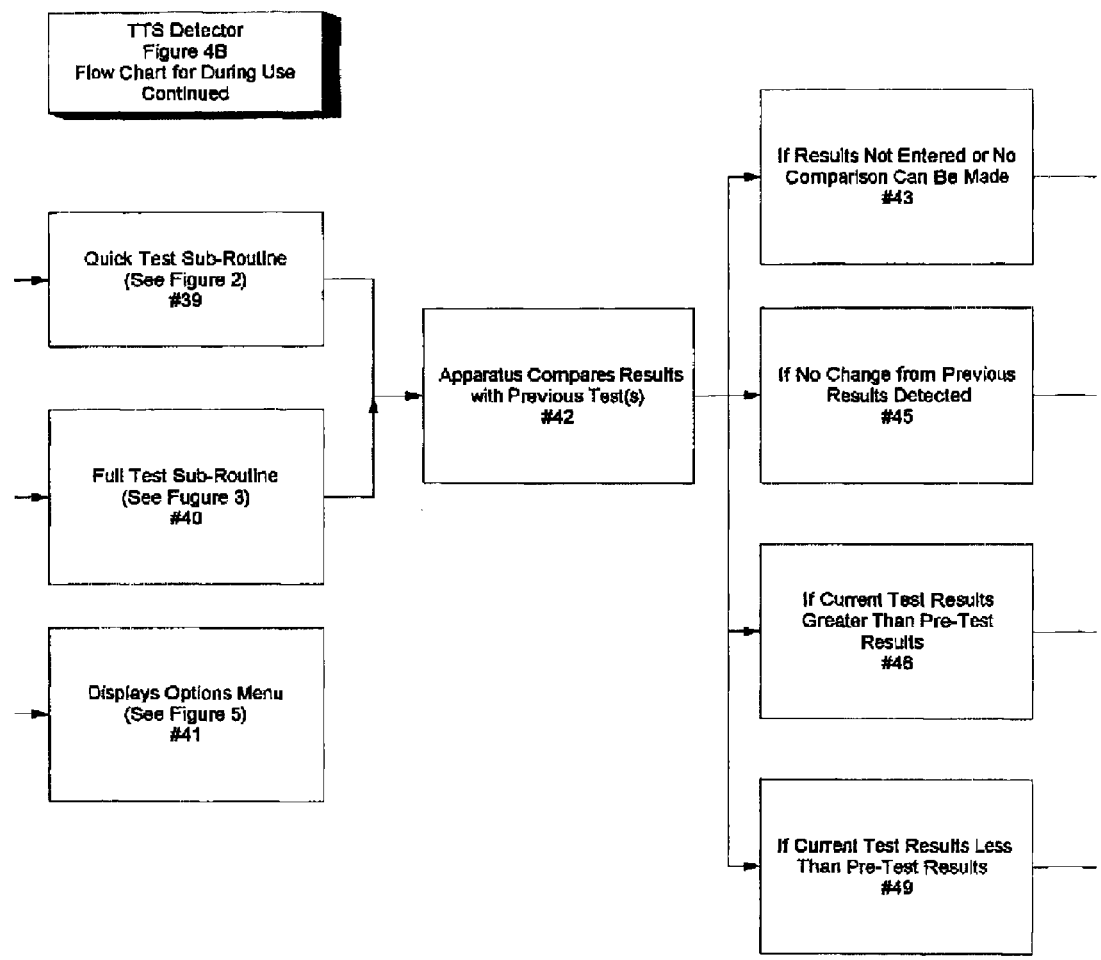

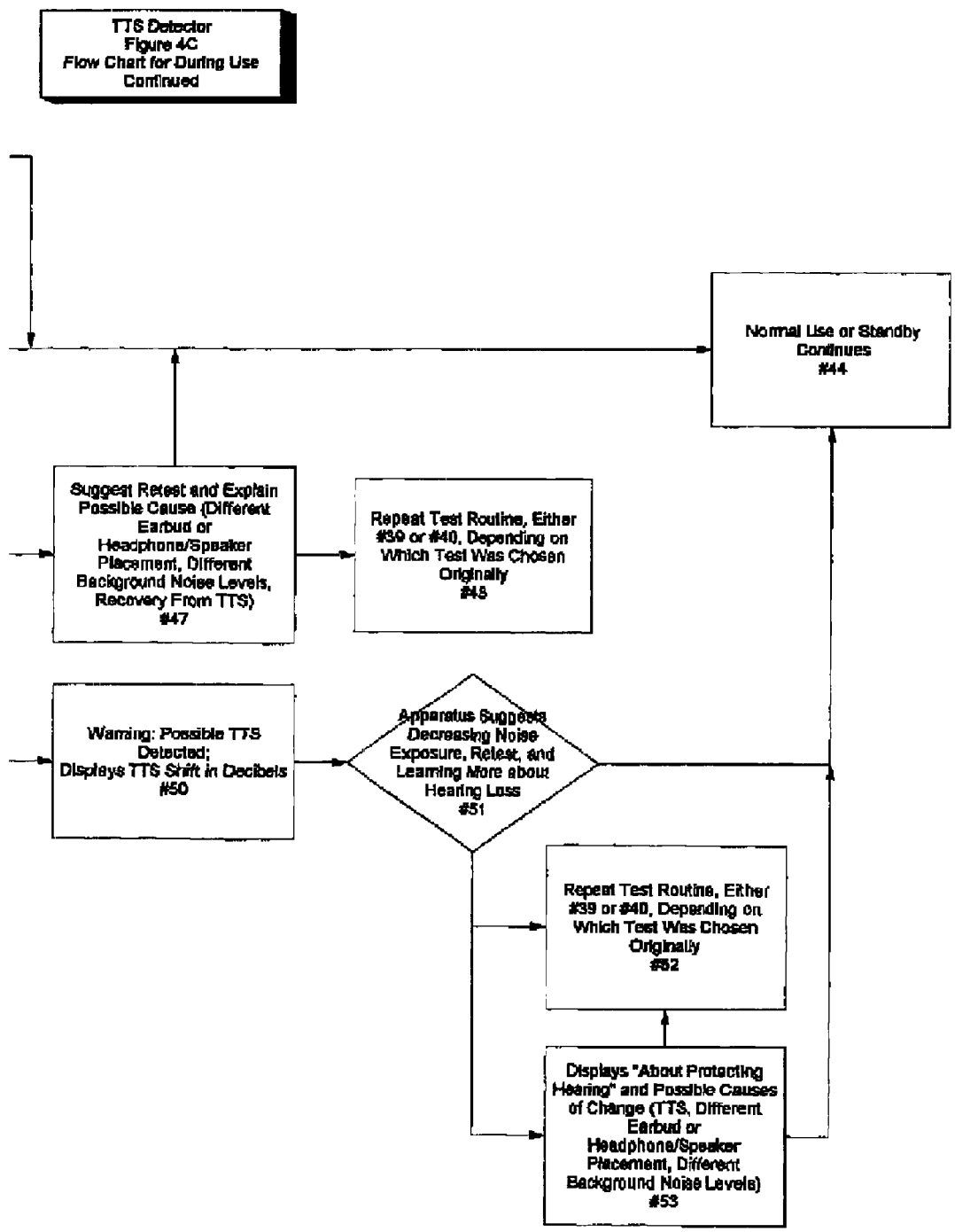

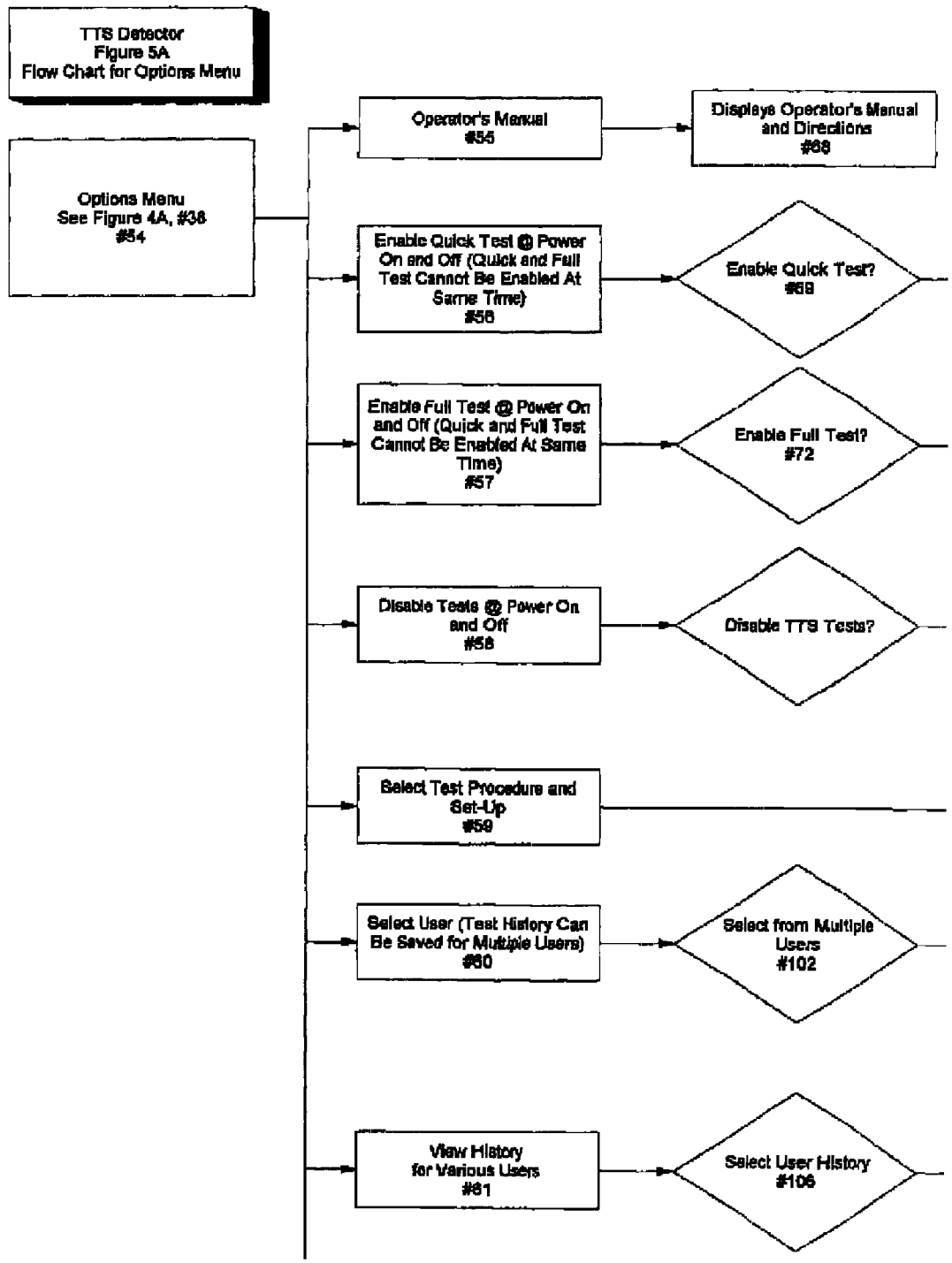

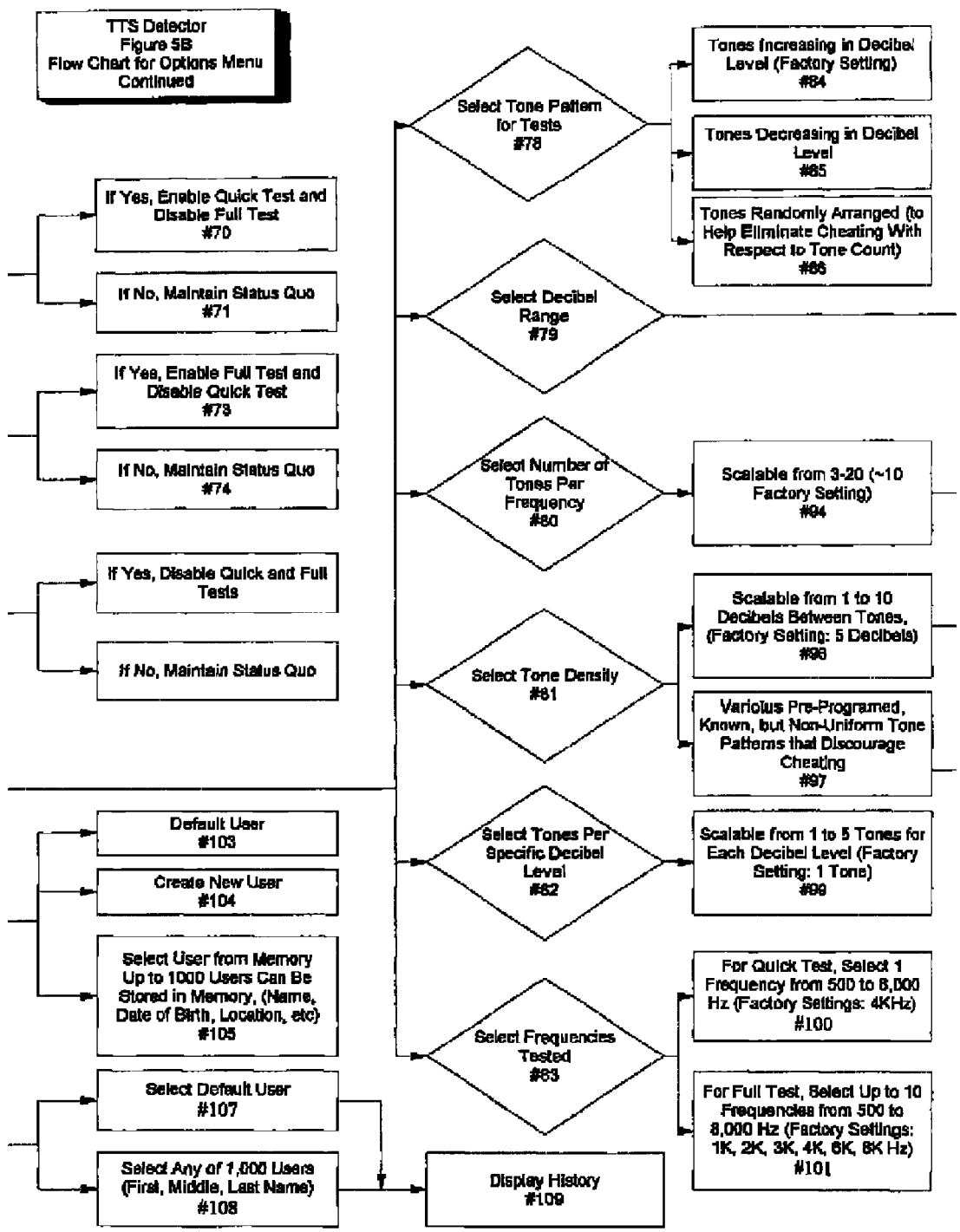

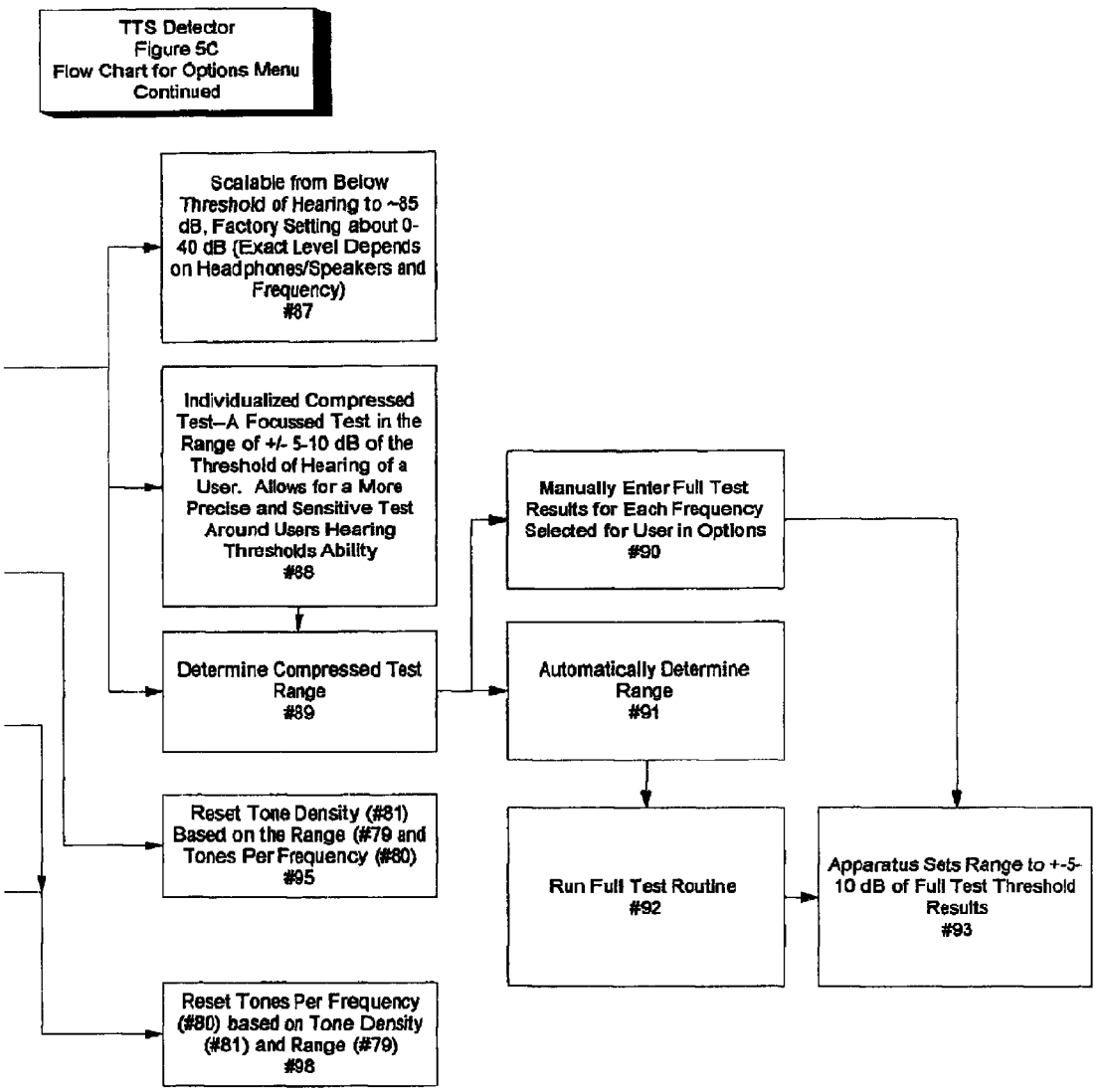

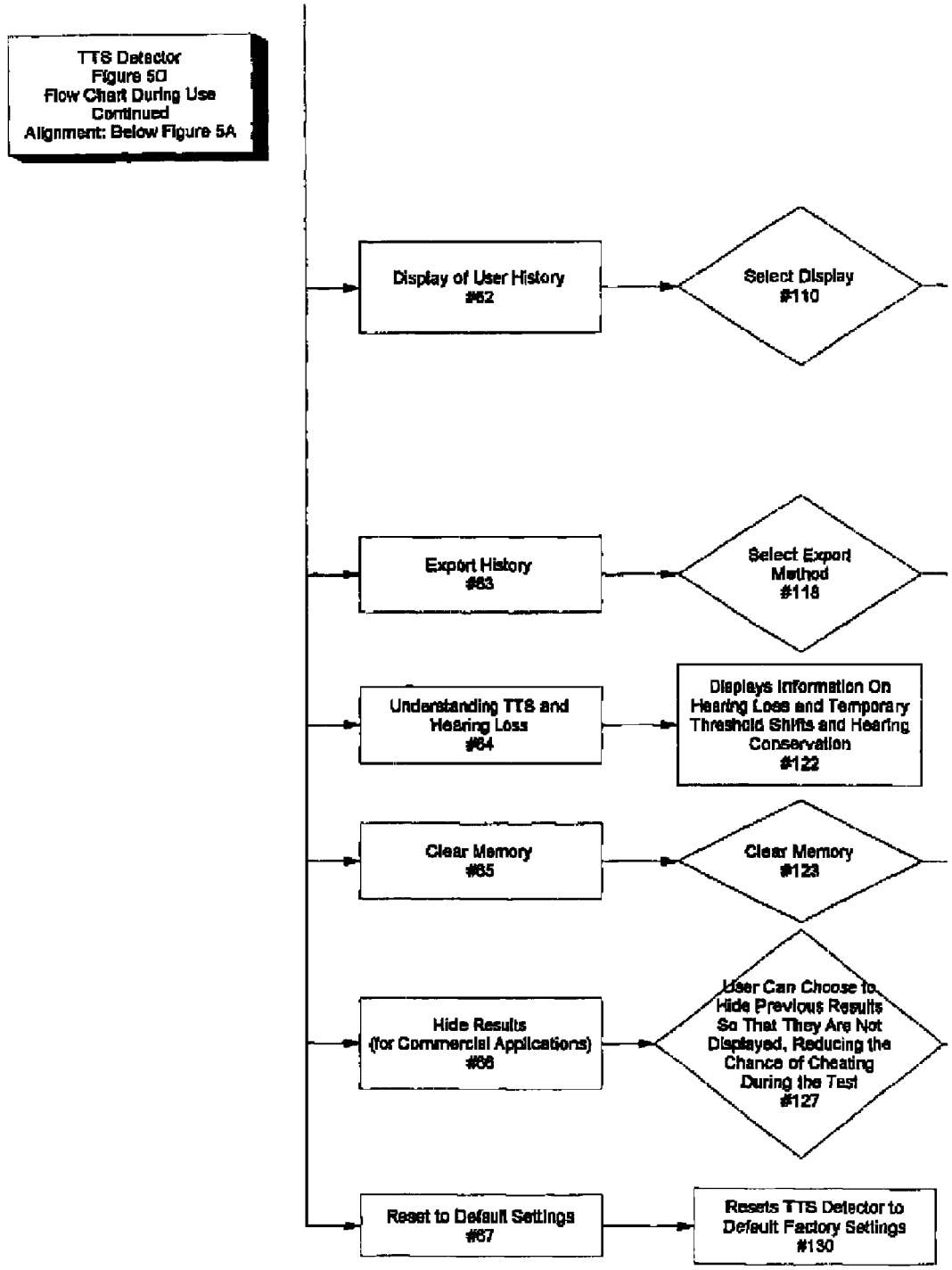

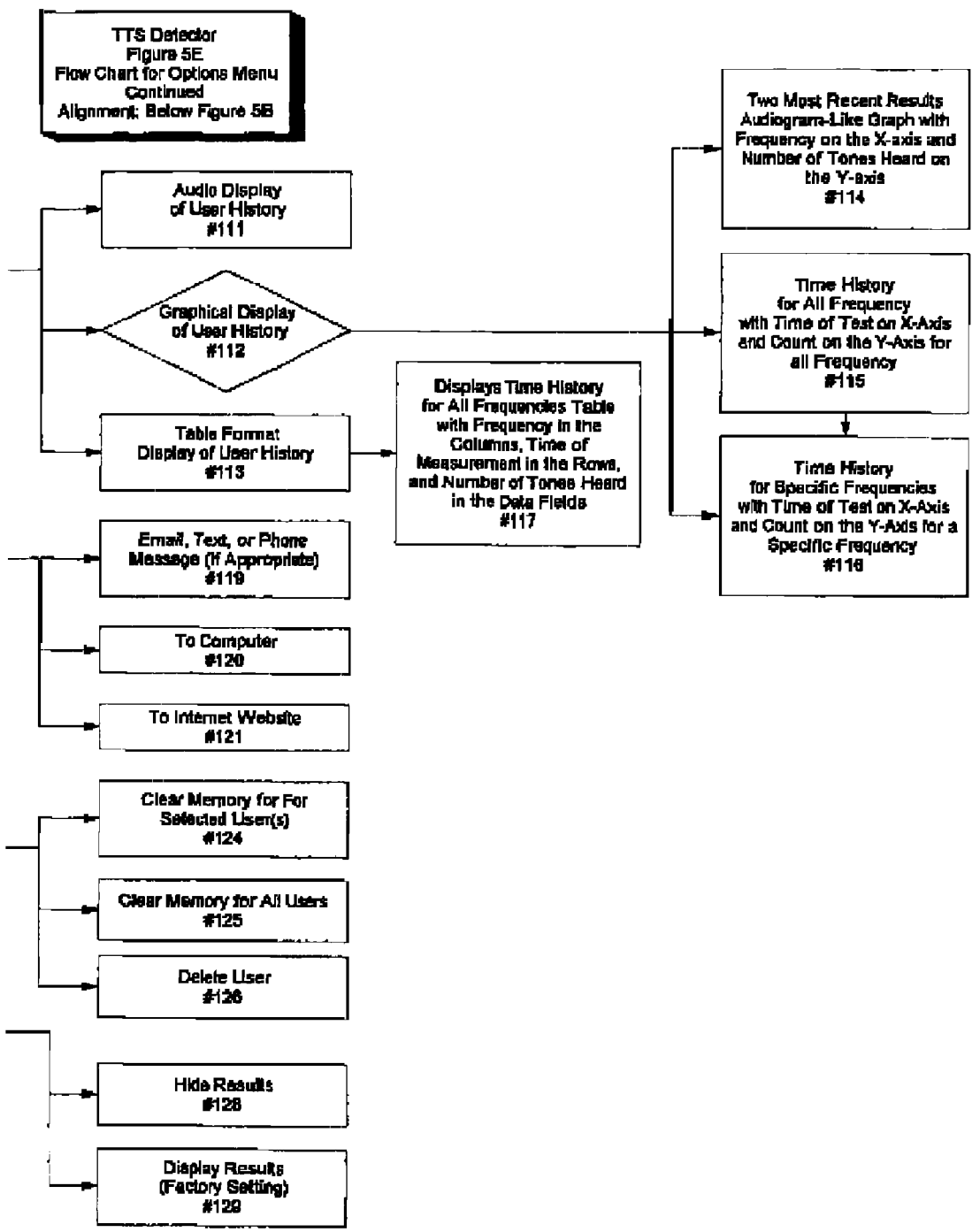

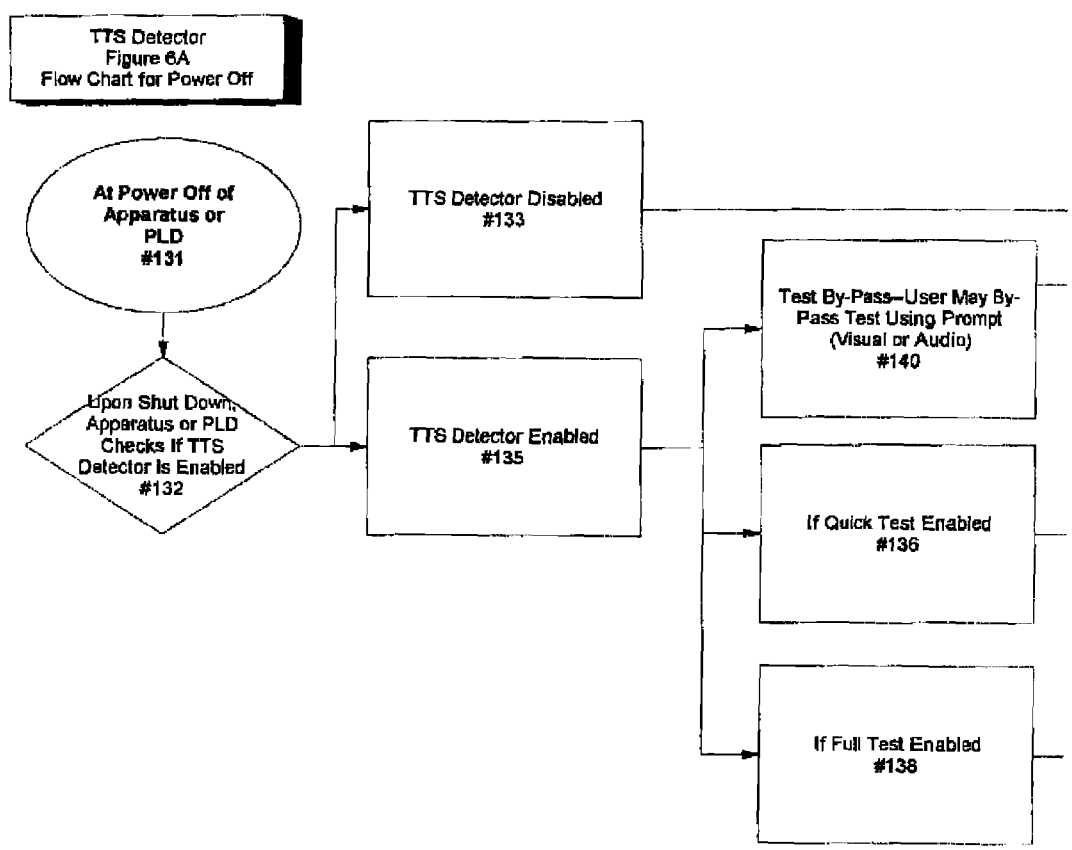

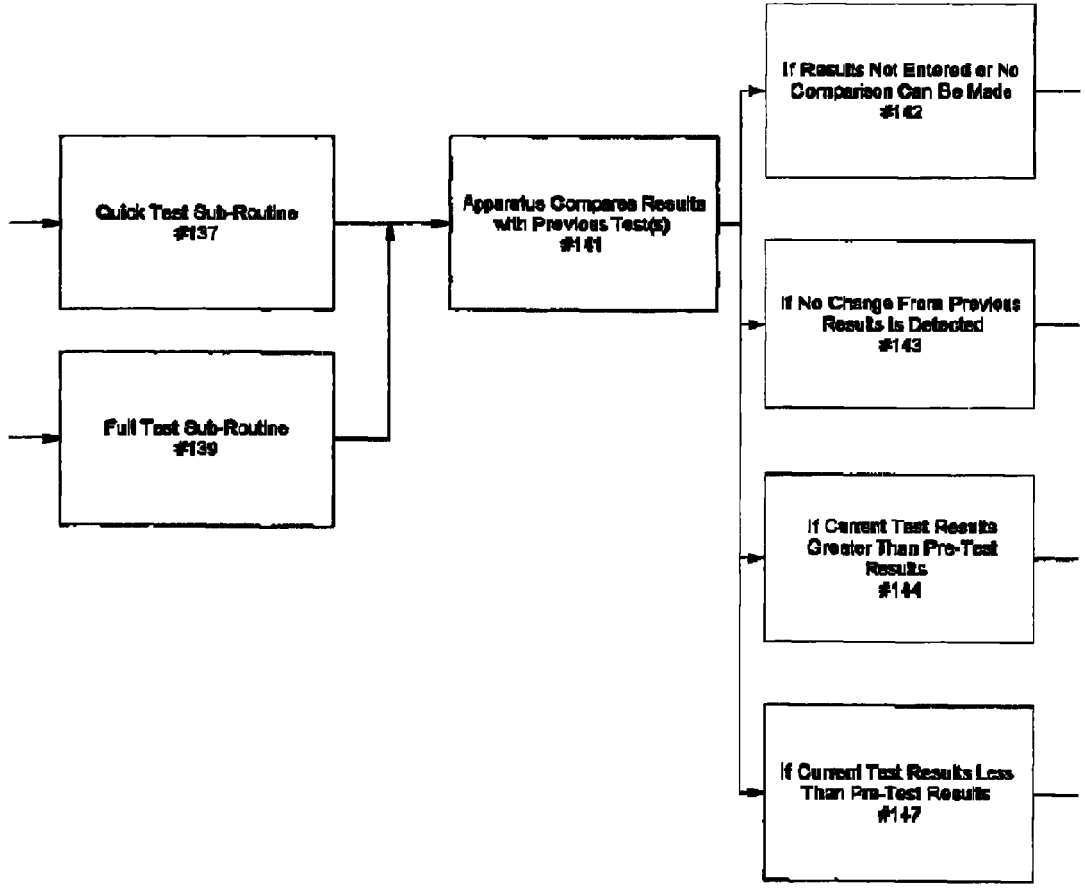

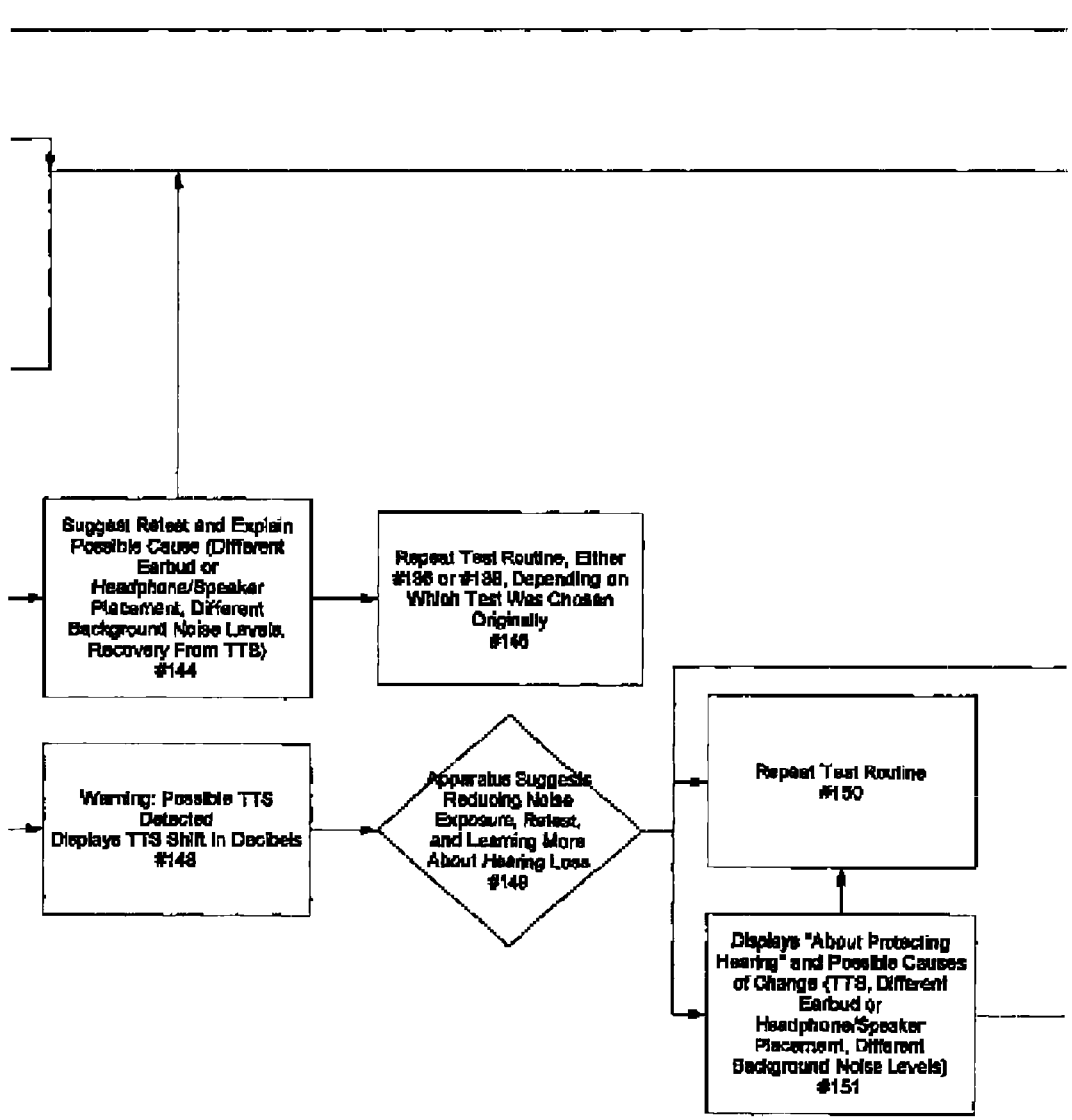

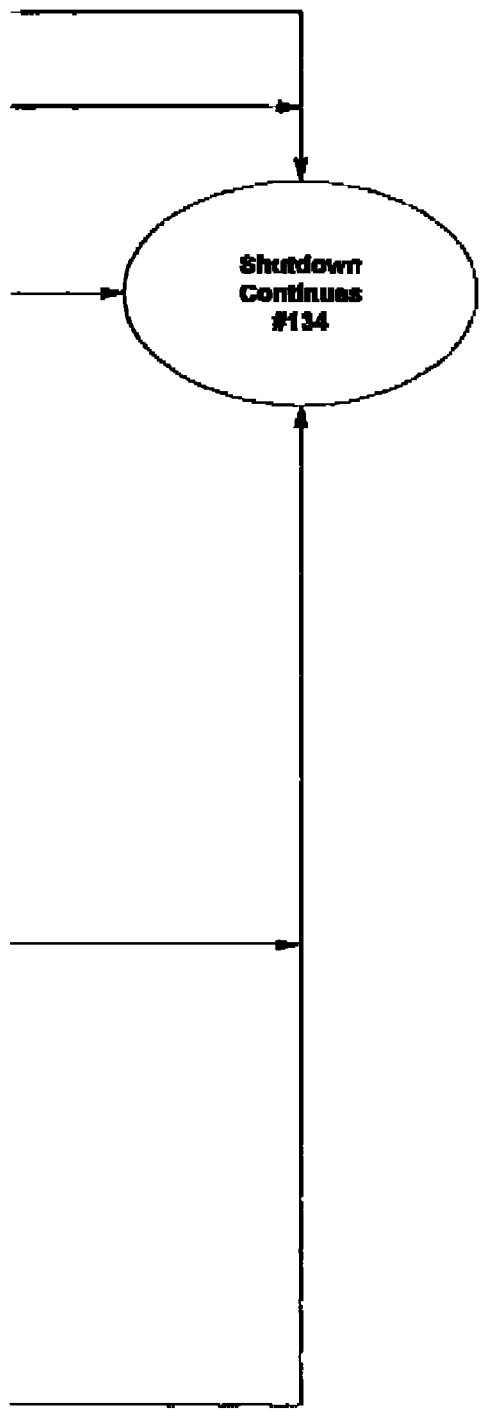

SOUND GENERATING DEVICE

TEMPORARY THRESHOLD SHIFT DETECTOR

RELATED APPLICATIONS AND PRIORITY

This application claims priority of Provisional Patent Application 60/816,839, filed Jun. 27, 2006, incorporated herein by reference.

FIELD

This patent application generally relates to testing hearing. More particularly it relates to a scheme for providing a hearing test with common electronic personal listening devices. Even more particularly it relates to a scheme for testing hearing and providing a warning if the listener experiences temporary hearing loss.

BACKGROUND

Members of the general public who use such noisy products as iPods and other personal listening devices usually do not know when the noise or music is so loud that hearing loss may result. Professionals rely on a complicated relationship between sound levels and time of exposure to determine risk of hearing loss. But accurately measuring sound levels has required equipment costing thousands of dollars. Members of the public have not had an adequate indicator of the line between safe and unsafe exposure, since they have neither the equipment, education, or experience in the area of hearing conservation. Since many of these members of the public who listen to personal listening devices are children a low cost and clear indicator of potential loss of hearing from a dangerous loudness level is particularly important.

Humans are able to hear sounds in frequencies between 20 Hertz to 20,000 Hertz. 20 Hertz is a very low frequency rumble that people might describe as a vibration; 20,000 Hertz is a very high frequency. The 88 keys on the piano range from 27.5 Hertz to 4186 Hertz. The loudness of a sound is generally given in decibels (although there are other measures). People normally hear from about 0 dB, the threshold of hearing, to 140 dB, a level that cause immediate hearing loss.

Most hearing loss occurs over time from repeated exposure to loud noise. Fewer hearing losses occur from a single exposure. The repeated exposure type of hearing loss manifests itself as a loss of hearing ability, often of the softest sounds at a particular frequency. The threshold of hearing, the softest sounds that are audible for each frequency, increases as hearing loss progresses. Changes in this threshold can either be a temporary threshold shift (TTS) or a permanent threshold shift (PTS).

U.S. Pat. No. 3,970,785 to Meyer, "Tone Count Audiometric Computer," filed May 13, 1975, and incorporated herein by reference, provides a hearing threshold level measuring apparatus for automatically determining testing hearing level in each ear and processing the test scores for either manual or automatic readout. A predetermined number of tone bursts varied randomly from one to four in each test sequence and automatically decreased in level. The subject is provided with a response panel containing pushbuttons labelled one through four. The subject's bearing threshold is then determined from his pushbutton responses to his correct burst tone counts.

U.S. Pat. No. 5,928,160 to Clark, "Home hearing test system and method" filed Oct. 30, 1996, and incorporated herein by reference, provides a home hearing test for use with a conventional home audio system comprising an audio player and a set of headphones connected to the audio player. The home hearing test includes an audio medium such as a compact disc playable in the audio player and containing a calibration tone recorded at a predetermined decibel level and a number of prerecorded sequences of tones. Each sequence has tones recorded at different decibel levels and decreasing by a step value. In a first sequence for obtaining a rough estimation of hearing threshold level, the tones start at 70 dB HL and decrease by 10 dB steps to 0 dB HL. In secondary sequences, tones start and end with tones from the first sequence and decrease in 2 dB steps. The home hearing system includes a calibration device for calibrating the output of the audio system to the ears of a person wearing the headphones against the predetermined decibel level of the calibration tone.

U.S. Pat. No. 6,350,243 to Johnson, "Portable hearing threshold tester" filed Dec. 29, 1999, and incorporated herein by reference, is a specialized portable hearing tester that provides pre-specified decibel levels to test the temporary hearing threshold shift of an individual. The portable hearing tester has a bone vibrator coupled to a discrete tone generator which is applied to a person's external skull. The bone vibrator is preferably gripped in the teeth. An alternative embodiment of the present invention uses a bone vibrator on the mastoid or forehead. The discrete tones generated through the bone vibrator can be heard by the person to test their current hearing threshold. Between 2 to 12 tones will be played for the person to hear. If the person cannot hear the selected tones at a specific decibel level which could be heard before, then that indicates a hearing threshold shift. Alternatively, discrete levels at one tone can be presented. The person need only count the number of distinct levels heard when the number of tones is reduced. When that number decreases it indicates a hearing threshold shift. The portable hearing tester can also include a two channel dosimeter which provides a way to eliminate a person's voice from the noise measurement.

SUMMARY

One aspect of the present patent application is an apparatus for testing hearing of a user. The apparatus includes a sound generating device for providing sounds at a plurality of fixed volume levels including a level above a threshold of hearing of the user and a level below a threshold of hearing of the user. Volume of sounds provided by the sound generating device are not field-calibratable. The apparatus also includes an input device connected for the user to enter data related to the hearing test. It also includes a memory connected for storing that data and a processor including a program for directing the sound generating device to provide the sounds. The processor is connected to the memory for comparing data entered at a first time with data entered at a second time. The apparatus also includes an output device connected to receive a result of the comparison from the processor. The output device is for providing the comparison hearing test result to the user.

Another aspect of the present patent application is a method of detecting a change in hearing of a user. The method comprises providing a sound generating device for providing both a content audio signal and a hearing test audio signal. The sound generating device is used to provide hearing test audio sounds of different loudnesses around a threshold of hearing of the user. None of these sounds is calibrated to a pre-specified decibel level. A first threshold of hearing is determined at a first time and a second threshold of hearing is determined at a second time. The first threshold of hearing is compared with the second threshold of hearing.

Another aspect of the present patent application is a method of detecting a change in hearing of a user. The method comprises providing sounds at a plurality of fixed volume levels at a first time, wherein the fixed volume levels include a level above a threshold of hearing of the user and a level below a threshold of hearing of the user. The sounds are not calibrated to pre-specified decibel values. Data related to the threshold of hearing at the first time is recorded. The sounds at the plurality of fixed volume levels are provided at a second time. Data related to the threshold of hearing at the second time is recorded. Threshold data entered at the first time is compared with threshold data entered at the second time. The comparison is used to determine whether a change in hearing has occurred.

Another aspect of the present patent application is a method of detecting a change in hearing of a user, comprising. The method comprises providing a device capable of providing both a content audio signal and a hearing test audio signal. A hearing test is automatically provided to the user when at least one from the group consisting of the device is switched on and the device is switched off but before the device turns off.

BRIEF DESCRIPTION OF THE DRAWINGS

FIGS. 1A and 1B connect to form a flow chart for a subroutine with user selectable settings for a hearing test at power on;

FIGS. 2A and 2B connect to form a flow chart for a quick hearing test subroutine;

FIGS. 3A and 3B connect to form a flow chart for a full hearing test subroutine;

FIGS. 4A-4C connect to form a flow chart for a sub-routine allowing a user to select a hearing test or go to the options menu during use of a listening device;

FIGS. 5A-5E connect to form a flow chart for a sub-routine allowing a user to select options from a menu;

FIGS. 6A-6D connect to form a flow chart for a sub-routine with user selectable settings for a hearing test at power off;

DETAILED DESCRIPTION

Figure 7A:
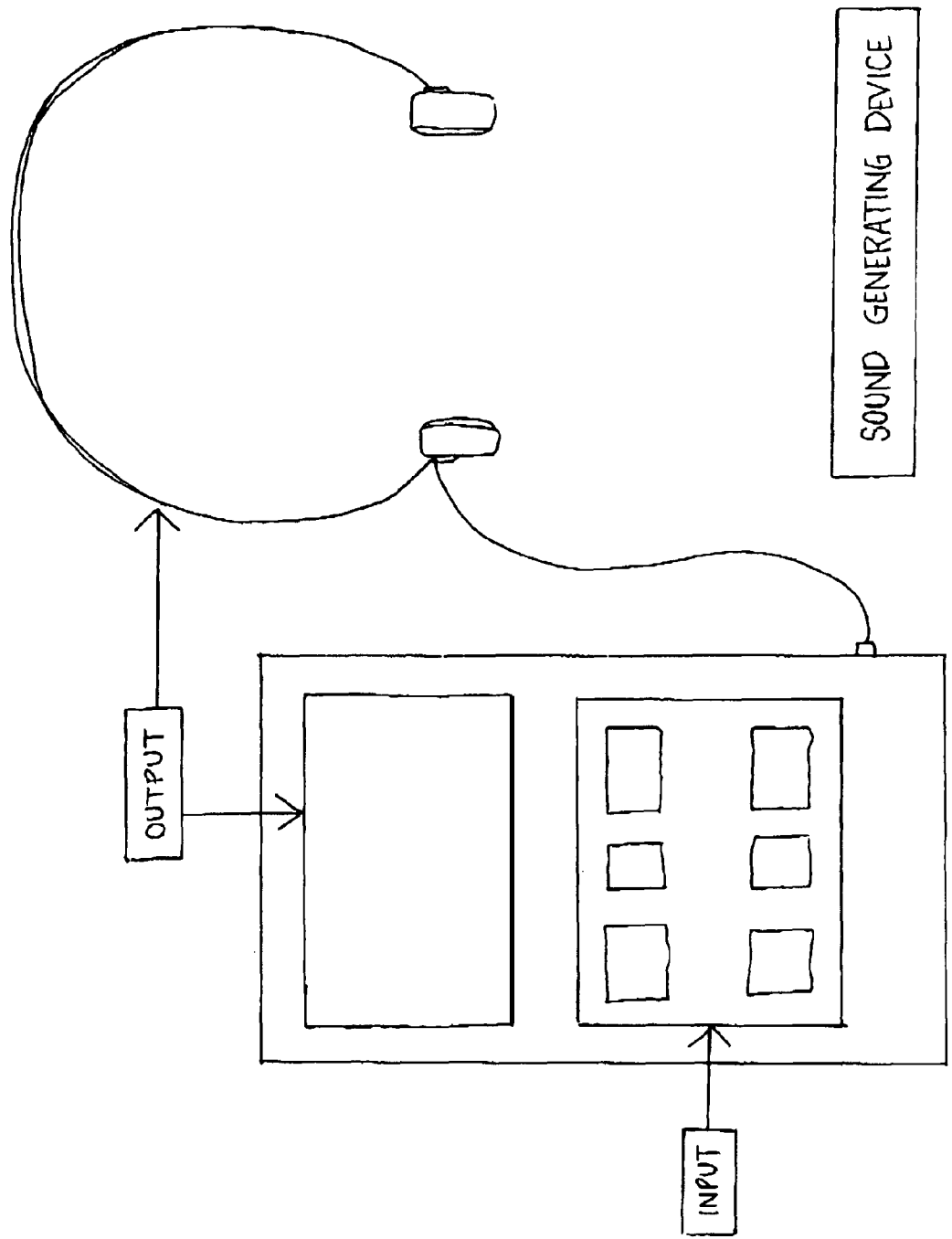
FIG. 7A is a schematic diagram of a sound generating device and a headset.

The Temporary Threshold Shift (TTS) Detector of the present patent application provides a hearing test that is useful with electronic devices, such as personal listening devices, sound reproduction devices, computers, and telecommunication devices. Such devices include an iPod, an MP3 device, a CD player, a tape player, a radio receiver, a phone, a Walkman, a Blackberry, a handheld computer, a headset and speakers. The telecommunications device can be a telephone, a cellular phone, a personal digital assistant, or a walkie talkie. The computer can be a laptop, desktop, hand held computer, a Palm Pilot, a Blackberry, a PDA, or a similar device. The device for providing the content audio signal and the hearing test signal can include a headset. The content signal can be a live source, prerecorded, or received from an external source.

One embodiment of the TTS Detector can be included in and can take advantage of personal listening devices, such as iPods, Walkmans, and MP3 players, to alert the user when noise levels of the devices pose a threat to their hearing health. The TTS Detector can also alert the user when other noises, such as work or recreation related noises, are potentially dangerous.

The TTS Detector allows people listening to personal listening devices or engaged in other noisy activities, either workplace related or recreational, to determine if their noise exposure is causing a temporary threshold shift so as to avoid repeated exposure that could lead to a permanent threshold shifts, a permanent decrease in hearing.

The TTS detector is based on the scientifically supported evidence that Permanent Threshold Shifts are preceded by Temporary Threshold Shifts and that TTS can be used as a predictor of permanent hearing loss. The invention detects if a noise exposure has caused a TTS and therefore, whether the noise exposure might lead to a PTS.

In traditional audiometry, testing for either TTS or PPS usually occurs at specific frequencies between 500 and 8,000 Hertz. At each frequency, a series of tones of known decibel levels are played for the testee, and he or she communicates to the tester whether specific tones are heard, allowing the tester to determine the threshold of hearing for that frequency. Recent research indicates that 500 Hertz testing is not necessary or useful in detecting hearing loss (because 1,000 Hertz basically gives the same results, but it is required by OSHA) and that noise induced hearing loss usually causes a "notch" or dip in hearing ability around 4,000 Hertz (frequencies around 4,000 Hertz are most effected by noise induced hearing loss). This testing is time consuming and identifies specific decibels levels of hearing ability at each frequency. Home tests often try to replicate audiological tests but have to incorporate expensive professional audiometric calibration techniques, such as calibrating sounds users hear to exact decibel levels, or accept inaccuracies from a technique, such as referencing to a normal hearer. The present application avoids the need to know the exact decibel level or to adjust the sound generating device to provide an exact decibel level. In the present application a change in hearing is determined without any of the sounds being calibrated by providing sounds both above and below the threshold of hearing that can be reliably reproduced at a subsequent test. If the number of sounds heard is the same then the user can conclude that no change in hearing occurred.

The present inventor recognized that tone counting was adequate for identifying a change in hearing threshold without the need or expense of identifying or calibrating to determine the decibel level of the tones. He recognized that this scheme allowed the test to be performed with personal listening devices that could not easily be accurately calibrated. In addition, he recognized that 4,000 Hertz was an important frequency for testing. And he recognized that starting and stopping of loud activities, such as listening to personal listening devices, were ideal times to test whether those activities were causing a temporary threshold shift.

The TTS Detector can be used to detect temporary threshold shifts caused by listening to personal listening devices. It can also be used with personal listening devices, sound reproduction devices, computers, hand computers, and telecommunication devices to detect TTS caused by other occupational or recreational noise sources.

The TTS Detector could operate with the standard earbuds or head phones supplied with the personal listening device. Noise reducing or canceling headsets or ear-plugs might be utilized to eliminate the effects of noisy background settings, but the device could also be used in quieter settings without consideration of background noise. Noise canceling or blocking headphones/earplugs systems can also address variations in results caused by variation in placement of the earbud/headphone.

One embodiment of the TTS Detector has the personal listening device provide a series of tones of increasing decibel level at a specific frequency that are played through the earbuds/headphones as the unit is powered on and off. The tones will play first in one ear, and then the other. A series of decreasing decibel level tones can also be used as can tones of different decibel levels in any other order. Each of the tones can last for a time equal to or less than one second. There can be period of silence separating the tones. Duration can be 2 seconds and typically the tones last for less than 5 seconds.

A tone ramping up or down in volume can also be used. In one such embodiment the user would press a button or otherwise signal the personal listening device the instant they first hear the tone as it ramps up in volume. The device would record this level. The user would repeat the test after a period of listening to the personal listening device or after experiencing other loud sounds. The sound level recorded from the second test would be compared with the level recorded in the first test to determine if there was a temporary threshold shift.

The decibel level of each tone and the specific frequency to be used can be adjusted by the user. In one embodiment 3-6 dB increments from about 10 dB below to about 40 dB above the threshold of hearing of typical users at a frequency in the range from about 3,000 to about 4,000 Hertz. In operation a user listens to and counts the tones. The personal listening device may be programmed to automatically provide the tones when it is turned on. The user would then again listen to and count the tones when the personal listening device is turned off and note any difference. For example, the user may be able to hear 5 tones before the noise exposure when turning on the personal listening device. If after listening the user is only be able to hear 4 tones they would know they suffered a TTS, and had been listening to the music at too high a level.

Figure 7B:
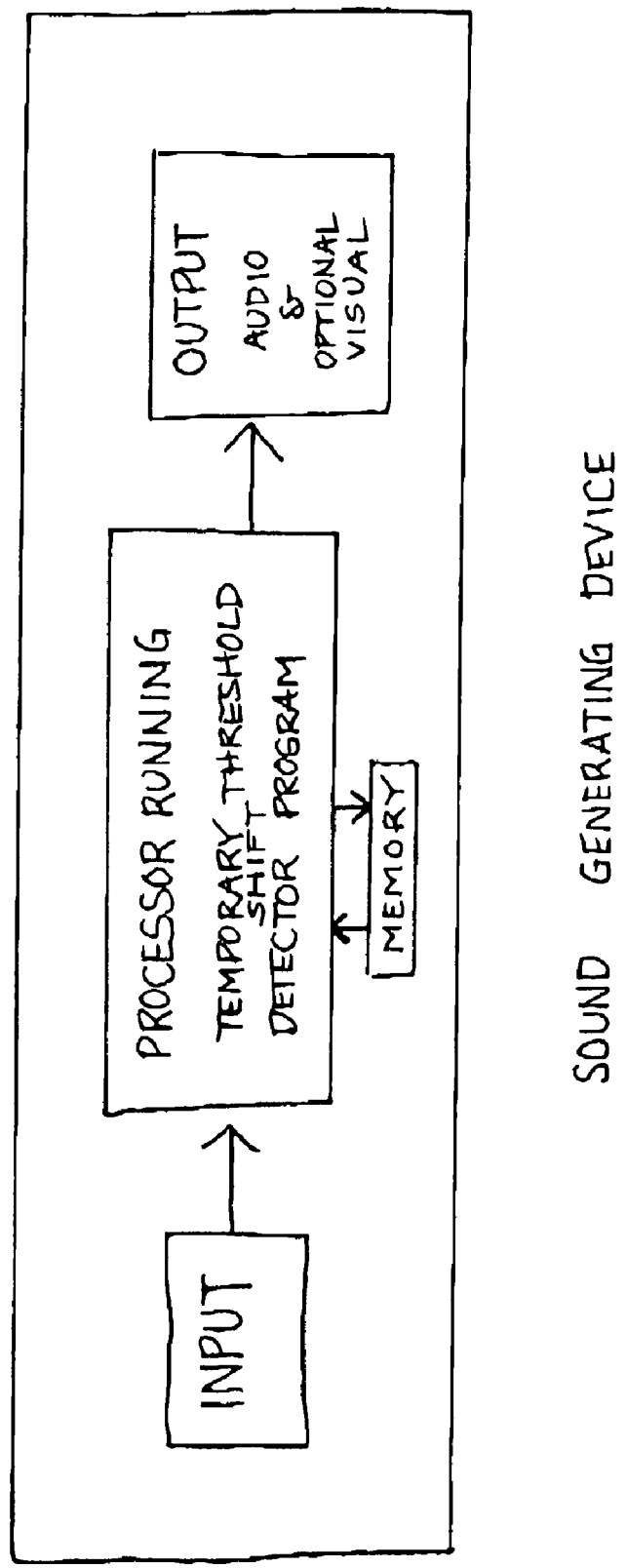
FIG. 7B is a block diagram of a sound generating device including an input, a processor, a memory, and an output.

In one embodiment the user just remembers the number of tones he or she heard for the before and after comparison. Pencil and paper can also be used for recording the data. If the personal listening device has an input device, such as keys, the user can enter the number of tones heard into the personal listening device before and after listening. Alternatively the user can press a button on the personal listening device to record hearing each tone as it is heard. The device can be programmed to record and display the number of tones heard by the user before and after use based on this input. Personal listening devices have substantial memory and a processor that can be used for this purpose, as shown in FIGS. 7A, 7B.

In addition to having the processor of the TTS Detector programmed to play its tones when powered on and powered off the user can select the tones for replay anytime after the unit is turned on. The tones can be provided in a file similar to the musical files the user may select on the personal listening device. The tones can also be generated from mathematical equations programmed into the device. In one embodiment the TTS tone generator operates to provide its tones with levels that are independent of the volume setting on the personal listening device. Personal listening devices, such as the iPod allow for this. The present applicant has programmed an iPod to save the current volume setting, then override the volume control, play the tones for the hearing test, and then reset the volume to the old setting. With those personal listening devices in which levels cannot be programmed, such as devices with analog control of the volume, the volume setting is set at the same level for the before and after tests.

A personal listening device, sound reproduction device, computer, hand computer, or telecommunication device can also be used to assess noise exposure from some other occupational or recreational noise source, including other personal listening devices. The user listens to and counts the number of tones played by the personal listening device before and after exposure to the occupational or recreational noise source to determine whether a threshold shift has occurred A more complete audiometric like test can also be provided using more frequencies and/or more decibel levels. The TTS detector for use with occupational and recreational noise sources would use a personal listening device, sound reproduction device, computer, hand computer, or telecommunication device to play tones at increasing or decreasing decibel levels at several frequencies such as 1,000, 2,000, 3,000, 4,000, 6,000 and 8,000 Hz. The tones would be played before and after exposure to noise, and the user would count the number of tones in each frequency range, entering the number into an interactive feature programmed into a personal listening device or other device that permits data entry. Pencil and paper can also be used for recording the data. A reduction in the number of tones at one of the frequencies from the exposure would demonstrate a threshold shift.

One aspect of the TTS detector hearing test is that it is not necessary to know or measure the decibel level of the threshold. Rather, a difference in the number of tones counted before and after exposure is measured, eliminating the need for costly calibration and measurement of sound pressure levels.

An output device, such as the audio or the display of the personal listening device, can be used to inform the user of the results of the hearing test.

Device at Power On

In use, the user turns on the Apparatus, as shown box #1 in FIGS. 1A, 1B. The apparatus may be a Personal Listening Device (PLD), such as an iPod, Walkman, and MP3 player. The Apparatus may also be any other sound reproduction device, such as a computer, a hand held computer, a video device, or a telecommunication device, such as a telephone.

The Apparatus resets to the selected settings of the default user, as shown in box #2. These settings are chosen in the Options menu, as shown in FIGS. 5A-5E, and as described below. The factory settings are used if they have not been changed or if this is the first start-up.

Upon start-up, the Apparatus checks to determine if the Temporary Threshold Detector (TTS Detector) is Enabled, as shown in box #3.

If the TTS Detector is Disabled, as shown in box #4, then start-up leads to normal use, as shown in box #5. Normal Use could include standby mode if the embodiment does not include combining the hearing test features with a personal listening device, sound reproduction device, computer, hand computer, or telecommunication device. Otherwise normal use could include playing music, computing, or telecommunicating.

If the TTS Detector is Enabled, as shown in box #6, then the apparatus checks to see if the Quick Test is enabled, as shown in box #7. This is the factory setting. If it is Enabled, then the Quick Test Sub-Routine is run, as shown in box #8. The Quick Test Sub-Routine is more fully described below under the description of FIG. 2, as shown in box #12-21, but the following provides a brief overview.

1. During the Quick Test Sub-Routine, a series of sounds is played in the left and then right ear as specified in the Options (FIG. 5).
2. The user either remembers the number of sounds heard or the number of sounds are entered into the apparatus, which remembers them.

After the Quick Test Sub-Routine is complete, the apparatus proceeds to Normal Use, as shown in box #5.

If the TTS Detector is enabled, as shown in box #6, and if the Full Test is enabled, as shown in box #9, (note: both the Quick Test and Full Test cannot be enabled at the same time) then the Full Test Sub-Routine is run, as shown in box #10. The Full Test Sub-Routine is more fully described below under the description of FIG. 3, as shown in box #22-#33; but the following provides a brief overview.

1. During the Full Test Sub-Routine, a series of sounds is played in the left and then right ear as specified in the Options (FIG. 5).
2. The user either remembers the number of sounds heard or the number of sounds are entered into the apparatus, which remembers them.

After the Full Test Sub-Routine is complete, the apparatus proceeds to Normal Use, as shown in box #5.

If the TTS Detector is enabled, as shown in box #6, the user may elect to by-pass the test, as shown in box #11. As the test occurs, the apparatus will also prompt users to by-pass the test if they choose. Since the apparatus may include many modern electronic devices such as personal listening devices, sound reproduction devices, computers, hand computers, or telecommunication devices, the prompts and interactions with the user may be audio or visual or both, depending on the nature of the device. Moreover, the responses of the user may be communicated to the apparatus by voice, touch screen, selecting displayed options or other manners appropriate for the device.

Quick Test Sub-Routine

At any time that the Quick Test Sub-Routine is called, as shown in box #12 of FIGS. 2A, 2B, the following occurs. The Apparatus plays a series of sounds in the left ear, as shown in box #13 as selected in Options (FIG. 5, box #59). The factory setting is to play approximately 10 tones at 3,000 or 4,000 hertz. These tones are not calibrated to a particular decibel level, but range from below the threshold of hearing for normal listeners in the frequency selected to about 40 (but possibly as many as 85 decibels) above that level. Since the decibel levels are not calibrated, these levels are only approximate levels, determined by identifying typical levels of typical users and typical Apparatus/speaker/headphone combinations. The levels of the tones should be independent of how the volume is set, and if this is not possible for some devices, should be at a consistent volume level for all tests.

Then the series of sounds are played in the right ear, as shown in box #14, as was the case in the left ear above.

While the sounds are being played, the Apparatus displays previous results, as shown in box #15, based on the setting in Options/Hide Results (FIG. 5, box #66). When the Apparatus is used by the general public, it is preferable that they know how many sounds they heard previously, so they immediately know if they have experienced a hearing impairment. When the Apparatus is used within industry, where TTS can be a test of the effectiveness of hearing conservation measures, there are greater concerns that cheating might occur. While it is very unlikely, to protect the integrity of a testing program it might be necessary to protect against workers who may wish to hide the fact that hearing loss has occurred, or may try to exaggerate that loss, in which case, knowing the results would aid in that effort.

Also during and after the sounds are being played, the apparatus prompts the user to enter the results, as shown in box #16. Results can be entered in a number of ways, including but not limited to:

1. As each sound is heard, a button can be pressed on the Apparatus.
2. After all the sounds are heard, the total number of sounds can be entered into the unit using a touch screen or menu selection.

If the results are entered in real time by pushing a button or otherwise indicating when specific tones are heard, the display of the results is also updated in real time.

If the user chooses not to enter the results, or if 3 seconds elapses, as shown in box #17, then the Quick Test Sub-Routine ends, as shown in box #18. The user must remember the number of tones heard or enter them manually into a hard copy Hearing Log.

If the user enters the tones heard into the Apparatus, as shown in box #19, then the Apparatus adds the time and date to and provides an opportunity for limited comments (type of noise, sound pressure level of noise, location, etc) to be added to memory. Then the Quick Test Sub-Routine ends, as shown in box #18.

An alternate user may also be selected, as shown in box #20. Select User (FIGS. 5A and 5B, box #60) is called, as shown in box #21. This option is described below, but briefly, it allows a new user to be created or one selected from memory. After a new user is created or selected, the user enters the tones heard into the Apparatus, as shown in box #19, then the Apparatus adds the time and date to and provides an opportunity for limited comments (type of noise, sound pressure level of noise, location, etc) to be added to memory. Then the Quick Test Sub-Routine ends, as shown in box #18. If the number of tones heard had been entered during the test, then the results are transferred to the new user by the Apparatus.

Full Test Sub-Routine

The Full Test Sub-Routine is very similar to the Quick Test, but more complicated because the test occurs at a plurality of frequencies. The Full Test Sub-Routine is basically the Quick Test repeated over several frequencies, first in the left ear, and then in the right ear.

At any time that the Full Test Sub-Routine is called, as shown in box #22 of FIGS. 3A, 3B, the following occurs. The Apparatus repeats the entire sub-routine for the frequencies selected in the Options Menu (see FIG. 5, box #101), first in the left ear and then in the right ear. The factory setting is to play 1,000, 2,000, 3,000, 4,000, 6,000, and 8,000 hertz first in the left and then in the right ear, as shown in box #23. The Apparatus plays a series of sounds, as shown in box #24 as selected in Options (FIG. 5, box #59). (The factory setting is to first play approximately 10 tones at 1,000 hertz in the left ear.) These tones are not calibrated to a particular decibel level, but range from below the threshold of hearing for normal listeners in the frequency selected to about 40 (but possibly as many as 85 decibels) above that level. Since the decibel levels are not calibrated, these levels are only approximate levels, determined by identifying typical levels of typical users and typical Apparatus/speaker/headphone combinations. The levels of the tones should be independent of how the volume is set, and if this is not possible for some devices, should be at a consistent volume level for all tests.

While the sounds are being played, the Apparatus displays previous results, as shown in box #25 based on the setting in Options/Hide Results (FIG. 5 #66). When the Apparatus is used by the general public, it is preferable that they know how many sounds they heard previously, so they immediately know if they have experienced a hearing impairment. When the Apparatus is used within industry to detect TTS, there are greater concerns that cheating might occur. While it is very unlikely, to protect the integrity of a testing program it might be necessary to protect against workers who may wish to hide the fact that hearing loss has occurred, or may try to exaggerate that loss, in which case, knowing the results would aid in that effort.

If there are many previous tests, how they are displayed will depend on the capacities of the apparatus and the options selected in Options/Display of User History (FIG. 5D, box #62). Depending on the capacities of the apparatus, it may be necessary to display only one result at a time, especially for the Full Test, since it will have several data points for several frequencies. Older test results may have to be viewed individually. (See Display of User History below for more information.)

Also during and after the sounds are being played, the apparatus prompts the user to enter the results, as shown in box #26. Results can be entered in a number of ways, including but not limited to:

1. As each sound is heard, a button can be pressed on the Apparatus.
2. After all the sounds are heard, the total number of sounds can be entered into the unit using a touch screen or menu selection.

If the user chooses not to enter the results, or if 3 seconds elapses, as shown in box #27, then the Apparatus checks to see if all the sounds at all the frequencies have been repeated, as shown in box #28. Since the user didn't enter the number of sounds, the user must remember the number or enter them manually into a hard copy Hearing Log.

If the user enters the tones heard into the Apparatus, as shown in box #29, then the Apparatus adds the time and date to and provides an opportunity for limited comments (type of noise, sound pressure level of noise, location, etc) to be added to memory. Then the Apparatus checks to see if all the sounds at all the frequencies have been repeated, as shown in box #28.

An alternate user may also be selected, as shown in box #30. Select User (FIGS. 5A and 5B, box #60) is called, as shown in box #21. This option is described below, but briefly, it allows a new user to be created or one selected from memory. After a new user is created or selected, the user enters the tones heard into the Apparatus, as shown in box #29, then the Apparatus adds the time and date as well as provides an opportunity for limited comments (type of noise, sound pressure level of noise, location, etc) to be added to memory. Then the Apparatus checks to see if all the sounds at all the frequencies have been repeated, as shown in box #28.

If the full test is not complete (if the routine has not repeated for all the appropriate frequencies in each ear) the sub-routine repeats over the next frequency, as shown in box #32.

If the full test is complete, the Full Test Sub-Routine ends, as shown in box #33.

Device During Use

At any time during the use of the Apparatus, as shown in box #34 of FIGS. 4A-4C, the user may select the TTS Detector from the Menu of the Apparatus, as shown in box #35. The user may select the Quick Test, as shown in box #36, the Full Test, as shown in box #37, or the Options Menu, as shown in box #38.

Selecting either the Quick or Full Test calls the Quick Test Sub-Routine, as shown in box #39 or the Full Test Sub-Routine, as shown in box #40 which are described above and shown in FIGS. 2 and 3. Selecting the Options Menu Displays the Options Menu; this will be fully described below and is shown in FIG. 5.

After the Quick Test Sub-Routine or Full Test Sub-Routine is complete (assuming either was chosen), the apparatus compares the results with previous tests, as shown in box #42. If the user did not enter any results, as shown in box #43, Normal Use or Standby Continues, as shown in box #44. If no change from the previous results is detected, as shown in box #45, then no TTS has been detected and the Apparatus returns to Normal Use or Standby, as shown in box #44.

If the current test results are greater than the previous test results, as shown in box #46, then it would appear that the user's hearing has improved. While this may represent a recovery from a TTS, this is most likely a false result, especially if it occurs after noise exposure. The Apparatus will suggest a retest and explain possible causes for the results such as different earbud, headphone, or speaker placement, different background noise levels, or recovery from TTS, as shown in box #47. The user may either retest, as shown in box #48 or continue to Normal Use or Standby, as shown in box #44. If retest is chosen, the Apparatus will rerun either the Quick Test Sub-Routine, as shown in box #39 or the Full Test Sub-Routine, as shown in box #40, depending on what was run originally. Operations #42 to #53 will then repeat as appropriate.

If the current test results are less than the previous test results, as shown in box #49, then the Apparatus displays a warning, that a possible TTS has been detected, as shown in box #50. The Apparatus, using the decibel difference in the sounds, will calculate and display the decibels the threshold has shifted by. The Apparatus will suggest immediately removing oneself from the noise exposure and decreasing noise exposure in the future, as shown in box #51. It will also suggest retesting, as shown in box #52 and learning more "About Protecting Hearing", as shown in box #53. "About Protecting Hearing" will primarily discuss how hearing works, how to protect hearing, and what the user should do to protect their hearing. Possible causes other than TTS will also be addressed, including different earbud, headphone, or speaker placement, different background noise levels, or recovery from TTS. A retest, as shown in box #52 will also be suggested. The user can also continue directly to Normal Use or Standby, as shown in box #44.

Options Menu

The Options Menu was discussed in reference to FIG. 4A, box #38 above and elsewhere. As this is the most complicated part of the flow chart, it is presented here independently.

The Options Menu presents 13 options, as shown in FIGS. 5A-5E. These include Operator's Manual, as shown in box #55, Enable Quick Test, as shown in box #56, Enable Full Test, as shown in box #57, Disable Tests, as shown in box #58, Select Test Procedure, as shown in box #59, Select User, as shown in box #60, View History, as shown in box #61, Select Display, as shown in box #62, Export History, as shown in box #63, Understanding TTS and Hearing Loss, as shown in box #64, Clear Memory, as shown in box #65, Hide Results, as shown in box #66, and Reset to Default Settings, as shown in box #67. The Options Menu allows users to customize the Apparatus to their needs and to view results. It also provides many features needed for commercial use of the Apparatus in hearing conservation applications.

The Apparatus comes with factory settings designed to meet the needs of many users. Each time the apparatus starts, as shown in box #1, it starts with the settings selected for the default user. This default user may be an actual individual (such as the owner of the Apparatus, or the default user might be a template for commercial or industrial applications so that it is easy to create new users with the same options profile.

Selecting the Operator's Manual, as shown in box #55 displays the Operator's Manual, as shown in box #68.

If Enable Quick Test, as shown in box #56 is selected, the Apparatus will ask the user to enable the Quick Test, as shown in box #69 at Startup and Shutdown. If the answer is yes, then the Quick Test is enabled and the Full Test is disabled, as shown in box #70. If the answer is no, then the status quo is maintained, as shown in box #71.

If Enable Full Test, as shown in box #57 is selected, the Apparatus will ask the user to enable the Full Test, as shown in box #72 at Startup and Shutdown. If the answer is yes, then the Quick Test is enabled and the Full Test is disabled, as shown in box #73. If the answer is no, then the status quo is maintained, as shown in box #74.

The Apparatus can also Disable TTS Tests, as shown in box #58 at Startup and Shutdown. The Apparatus will ask the user to disable the Quick and Full Tests, as shown in box #75 at Startup and Shutdown. If the answer is yes, then the Quick Test and Full Test is disabled, as shown in box #76. If the answer is no, then the status quo is maintained, as shown in box #77.

Select Test Procedure and Setup, as shown in box #59 is the most complicated Options Menu selection, since there are many ways to setup the Apparatus, covering many but not all embodiments of the invention. Conversely, some embodiments may not have all the features described below.

By selecting the fifth Menu Option, Test Procedure and Setup, as shown in box #59, the user is presented 6 setup choices or options: Select Tone Pattern, as shown in box #78, Select Decibel Range, as shown in box #79, Select the Number of Tones Per Frequency #80), Select Tone Density, as shown in box #81, Select Tones Per Decibel Level, as shown in box #82, Select Frequencies Tested, as shown in box #83.

Select Tone Patterns for Tests, as shown in box #78 allows the user to choose from sounds that are increasing in decibel level, as shown in box #84, decreasing in decibel level, as shown in box #85, or random, as shown in box #86. The increasing in decibel level, as shown in box #84 is the factory setting. The hope is that informed and concerned users will quickly learn how many tones they hear and will immediately recognize if they have suffered a TTS. The random setting, as shown in box #86 is to minimize the possibility of cheating in a commercial or industrial setting where it is unlikely but conceivable that someone would want to under- or overstate their hearing loss or ability. Since the sounds would be randomly played, and if the user pressed the button every time they claimed to have heard the sound, it is very likely that there will be a "gap" in the sounds heard—that sounds at decibel levels above the lowest level heard will "not" be heard. This information will be available to the user or administrator in the Display History and Export History sections described below (FIG. 5).

Select Decibel Range, as shown in box #79 allows the user to determine the decibels between the quietest and loudest sounds. The first option is to set those levels, as shown in box #87 from slightly below the threshold of hearing for average listeners to about 85 decibels. The factory setting is from the threshold to about 40 decibels above the threshold. Since the exact decibel level is not known, and varies with speakers/headphones/earbuds, these are approximate values based on typical equipment supplied with the apparatus. The levels are scaleable, with a user able to choose the beginning and ending value between 0 and 85 decibels. The advantage of using a narrower range is that for the same number of sounds, the precision of the Apparatus increases (the Apparatus is able to detect smaller threshold shifts). (Note: With increasing sensitivity, the Apparatus needs more consistent testing conditions such as background noise and relationship between speaker and ear.)

The precision and sensitivity of the Apparatus can be further increased by selecting the Individualized Compressed Tests, as shown in box #88. The Compressed Test focuses the test tightly around the individual's threshold of hearing for each frequency tested. In some embodiments, this will be the preferred setting. For the general public, however, it might be better if all users have the same factory setting so that they can easily compare their results to other's results or use another's Apparatus. The Individualized Compressed Test, as shown in box #88 requires that the user first Determine the Compressed Test Range, as shown in box #89. This can be done either Manually, as shown in box #90 or Automatically, as shown in box #91. The manual option requires that the user enter the number of sounds heard using either factory setting Quick or Full Test results. Most users will choose to let the Apparatus determine their threshold of hearing by running the Full Test Routine, as shown in box #92 and pressing the appropriate button each time the sound is heard. After the results are either manually entered or automatically determined, the Apparatus then sets the range to about plus or minus 5-10 of the thresholds, as shown in box #93.

The next two Setup Options, as shown in box #80 and #81 are not logically independent. They involve ways of controlling the sensitivity of the Apparatus by specifying how many tones are played or how close together those tones are. After setting the Range, as shown in box #79, setting either the Number of Tones, as shown in box #80 or the Density, as shown in box #81 will reset the other. The Apparatus will automatically recalculate the new value (see #95 and #98 below).

Select Number of Tones per Frequency, as shown in box #80 provides a scalable range from 3-20 tones that can be played for each frequency, as shown in box #94. Controlling the number of tones per frequency is one way of controlling the sensitivity of the Apparatus. Select Decibel Range, as shown in box #79 above) allows the user to narrow the range that the tones cover, Select Number of Tones per Frequency, as shown in box #80 allows the user to increase (or decrease) the number of tones. More tones (as well as a smaller range) result in a more precise identification of hearing thresholds and shifts, just as a ruler marked in inches can give a more precise measure than one marked only in feet. However, more tones require more time to take the test and may discourage use by some voluntary users. The factory setting is approximately 10 tones. Tone Density, as shown in box #81 will be recalculated, as shown in box #95 based on the settings in Range, as shown in box #79 and Tones per Frequency, as shown in box #80.

Select Tone Density, as shown in box #81 provides the second way to control the sensitivity of the Apparatus. Select Tone Density, as shown in box #81 allows the user to choose between a scalable decibel difference between tones that range from 1 to 10 decibels, as shown in box #96 and a set of pre-programmed non-uniform (linearly speaking—they could be logarithmic or exponential) tone patterns, as shown in box #97 that are designed to discourage cheating in certain commercial applications. Selecting Density, as shown in box #81 will recalculated and reset, as shown in box #98 the settings in Tones per Frequency, as shown in box #80 based on the Range, as shown in box #79.

Select Tones Per Decibel Level, as shown in box #82 is another options menu item, and should not be confused with Tones per Frequency. At each frequency, whether part of the Quick or Full Test, a series of tones of different decibel levels are played. The tone at a particular decibel level can be repeated up to 5 times as allowed for in the scalable menu, as shown in box #99. The factory setting is one tone to shorten the time required to take the test.

Select Frequencies Tested, as shown in box #83 allows the user to select both the Quick Test Frequency, as shown in box #100 or the Full Test Frequencies, as shown in box #101. The Quick Test frequency can be between 500 and 8,000 Hz, as shown in box #100. The factory setting is either 3,000 or 4,000 Hz. The Full Test allows the user to choose up to 10 frequencies between 500 and 8,000 Hz. The factory setting is 1,000, 2,000, 3,000, 4,000, 6,000, 8,000 Hz.

This concludes the Select Test Procedure and Setup, as shown in box #59 for a wide selection of embodiments of the Apparatus. Not all test procedures need to be included in every embodiment, and some embodiments may have additional setup features.

The sixth Options Menu, as shown in box #54 is Select User, as shown in box #60. Select User, as shown in box #60 allows for multiple users of the Apparatus. Select User provides 3 options, as shown in box #102: Default User, as shown in box #103; Create New User, as shown in box #104; and Select User from Memory, as shown in box #105. The Default User is designed primarily for the single user of the Apparatus, and is the user and options profile that appears when the unit is first turned on. If there is more than one user, they may use Select User, as shown in box #60 to create a New User, as shown in box #104 or a new profile for a user. Information that may be entered into memory identifying the user may include their name, work station or location, employee ID, etc. Select User from Memory, as shown in box #105 allows operators to switch between different users. Each user Options Menu selections creates a user profile that is stored in memory, so when ever a specific user is selected, so is the Test Procedure and Set-Up conditions.

View History, as shown in box #61 is the seventh Menu Option. View History, as shown in box #61 provides 2 options, as shown in box #106: it allows the user to select between viewing results for the Default User, as shown in box #107 or to select any of the 1,000 users from memory, as shown in box #108. When a user is selected, their results are displayed, as shown in box #109 in accordance with criteria in Display of User History, as shown in box #62 which is described below.

Display of User History, as shown in box #62 is the eighth Menu Option. It and the remaining Menu Options can be found on FIGS. 5D and 5E, which should be aligned immediately below FIGS. 5A and 5B respectively. Display of User History, as shown in box #62 provides 3 options, as shown in box #110: it allows the user to select between Audio, as shown in box #111, Graphical, as shown in box #112, or Table Format, as shown in box #113 Display of User History. Not all of these options will be appropriate for all embodiments of the Apparatus (telecommunications equipment, for example, may not have graphical or table display capability.

In addition to the features described below (which involve different ways of telling the user how many tones they heard at different times and frequencies), each of the display modes will also display the decibel difference between the tones, so that users can judge the size of any threshold shift that occurred.

The display of some embodiments are more complex than described below, such as if the decibel difference between the tones is not uniform (see Pre-Programmed Non-Uniform Tone Patterns, #97, below). Also, if the user changes Test Procedures and Setup features (perhaps the user might change the frequencies tested, for example) then only the tests since the last change will be displayed, although the older data will be available using the Export History function.

The Audio Display, as shown in box #111 informs the user of results including frequency and number of tones heard, and the time and date of the measurement using the speaker system of the Apparatus.

The Graphical Display, as shown in box #112 provides 3 options. The first graphical option allows the user to display the previous results and the current results in an audiogram-like display with Frequency on the X-axis and number of tones heard on the Y-axis, as shown in box #114. There will be 2 lines in the case of the Full Test and 2 bars in the case of the Quick Test. Assuming that the tones heard are entered by pressing a button when they are heard, the results will be updated in real time. Changes in threshold will be easily seen by comparing the 2 lines.

The second graphical display option allows the user to Display the Time History for All Frequencies, as shown in box #115 with Time on the X-axis and Number of Tones Heard on the Y-Axis. This graph could be quite complicated (depending on the number of frequencies tested) and will require multiple lines (one for each frequency tested). Changes in threshold will be detected by deviations from horizontal lines.

The third graphical display option is to display the Time History for Specific Frequencies, as shown in box #116. This may be done by either selecting a Specific Frequency, as shown in box #116 from those tested or selecting a specific frequency from the graph of All Frequencies, as shown in box #115. The display in #116 will look like a simplified version of #115, with only one frequency displayed at a time. In addition, #116 will provide the ability of the user to select and view other frequencies.

The third Display of User History, as shown in box #62 choice is a Table Format, as shown in box #113. This Displays Time History, as shown in box #117 for All Frequencies in a table with Frequency in the Columns, Time of Measurement in the Rows, and Number of Tones Heard in the Data Fields. This function displays all the data in #115 in a table format. Some embodiments of the Apparatus with limited or no viewing screen may have to limit the information displayed.

Export History, as shown in box #63 is the ninth Menu Option. Export History, as shown in box #63 provides 3 options, as shown in box #118: it allows the user to send results by either email, text, or phone messages, as shown in box #119; to a computer in spreadsheet or database formats, as shown in box #120, or to an internet website or network location, as shown in box #121.

Understanding TTS and Hearing Loss, as shown in box #64 is the tenth Menu Option. It displays text written by an expert in the field of hearing conservation concerning TTS, hearing loss, and hearing protection, as shown in box #122.

Clear Memory, as shown in box #65 is the eleventh Menu Option. Clear Memory, as shown in box #65 provides 3 options, as shown in box #123: it allows the operator to clear the memory for selected users, as shown in box #124; to clear the memory for all users, as shown in box #125; or to delete users, as shown in box #126. (It is not possible to delete the default user). Operators are asked if they are sure they want to delete user or clear memory before the memory is altered.

Hide Results, as shown in box #66 is the twelfth Menu Option. Hide Results, as shown in box #66 provides 2 choices, as shown in box #127: Hide Results, as shown in box #128 or Display Results, as shown in box #129. The primary use of Hide Results is to discourage cheating in commercial or industrial hearing conservation programs. There may be many commercial or industrial uses for which this is not necessary, and it is preferred that results always be displayed.

Reset to Default Settings, as shown in box #67 is the thirteenth Menu Option. It resets the Options Menu settings, as shown in box #54 for the selected user to the factory or default settings, as shown in box #130.

Additional Options may be available in other embodiments of the Apparatus, and not all options described above will be available in all embodiments. One option that may be available on some embodiments is adjusting the length of time of the sound played and the silence between sounds. The embodiment described here uses tones of at a certain frequency. The length of the tones and silence are set at the factory at 200 ms for the tone and 100 ms for the silence, but many other settings are possible and could be used or incorporated as another Test Procedure and Set-Up option.

Device at Power Off

The user turns off the Apparatus, as shown in box #131 of FIGS. 6A-6D.

Upon Shutdown, the apparatus checks to determine if the Temporary Threshold Detector (TTS Detector) is Enabled, as shown in box #132.

If the TTS Detector is Disabled, as shown in box #133, then shutdown continues, as shown in box #134.

If the TTS Detector is enabled, as shown in box #135, then the apparatus checks to see if the Quick Test is enabled, as shown in box #136. This is the factory setting. If it is enabled, then the Quick Test Sub-Routine is run, as shown in box #137. The Quick Test Sub-Routine is described formally and more fully above in the Description of FIG. 2, as shown in box #12-21; but the following provides a brief Overview.

1. During the Quick Test Sub-Routine, a series of sounds is played in the left and then right ear as specified in the Options (FIG. 5).
2. The user either remembers the number of sounds heard or the number of sounds are entered into the apparatus, which remembers them.

If the TTS Detector is enabled, as shown in box #134, and if the Full Test is enabled, as shown in box #138, (note: both the Quick Test and Full Test cannot be enabled at the same time) then the Full Test Sub-Routine is run, as shown in box #139. The Full Test Sub-Routine is described formally and more fully above in the Description of FIG. 3, as shown in box #22-#33; but the following provides a brief Overview.

1. During the Full Test Sub-Routine, a series of sounds is played in the left and then right ear as specified in the Options (FIG. 5).
2. The user either remembers the number of sounds heard or the number of sounds are entered into the apparatus, which remembers them.

If the TTS Detector is enabled, as shown in box #135, the user may elect to by-pass the test, as shown in box #140. As the test occurs, the apparatus will also prompt users to by-pass the test if they choose. Since the apparatus may include many modern electronic devices such as personal listening devices, sound reproduction devices, computers, hand computers, or telecommunication devices, the prompts and interactions with the user may be audio or visual or both, depending on the nature of the device. Moreover, the responses of the user may be communicated to the apparatus by voice, touch screen, selecting displayed options or other manners appropriate for the device.

After the Quick Test Sub-Routine or Full Test Sub-Routine is complete, the apparatus compares the results with previous tests, as shown in box #141. If the user did not enter any results, as shown in box #142, Shutdown Continues, as shown in box #134. If no change from the previous results are detected, as shown in box #143, then no TTS has been detected and the Apparatus Continues Shutdown, as shown in box #134.

If the current test results are greater than the previous test results, as shown in box #144, then it would appear that the user's hearing has improved. While this may represent a recovery from a TTS, this is most likely a false result. The Apparatus will suggest a retest and explain possible causes for the results such as different earbud, headphone, or speaker placement, different background noise levels, or recovery from TTS, as shown in box #145. The user may either retest, as shown in box #146 or continue to shutdown, as shown in box #134. If retest is chosen, the Apparatus will rerun either the Quick Test Sub-Routine, as shown in box #137 or the Full Test Sub-Routine, as shown in box #139, depending on what was run originally. Operations #141 and forward will then repeat as appropriate.

If the current test results are less than the previous test results, as shown in box #147, then the Apparatus displays a warning, that a possible TTS has been detected, as shown in box #148. The Apparatus, using the decibel difference in the sounds, will calculate and display the decibels the threshold has shifted by. The Apparatus will suggest immediately removing oneself from the noise exposure and decreasing noise exposure in the future, as shown in box #149. It will also suggest retesting, as shown in box #150 and learning more "About Protecting Hearing", as shown in box #151. "About Protecting Hearing" will primarily discuss how hearing works, how to protect hearing, and what the user should do to protect their hearing. Possible causes other than TTS will also be addressed, including different earbud, headphone, or speaker placement, different background noise levels. A retest, as shown in box #150 will also be suggested. The user can also continue directly to Shutdown, as shown in box #134.

While the disclosed methods and systems have been shown and described in connection with illustrated embodiments, various changes may be made therein without departing from the spirit and scope of the invention as defined in the appended claims.

The invention claimed is:

1. A method of detecting a change in hearing of a user, comprising:
   a. providing an electronic sound generating device for providing a content audio signal, wherein said electronic sound generating device includes a hearing test audio signal, wherein said hearing test audio signal includes sounds at a plurality of volumes, including sound having a volume below a threshold of hearing of the user and sound having a volume above a threshold of hearing of the user, wherein volume of none of said sounds is measured, and wherein said electronic sound generating device is capable of reproducing said hearing test audio signal with sounds having same unmeasured volume at a subsequent time;
   b. using said electronic sound generating device to produce said hearing test audio signal at a first time;
   c. determining a first measure of threshold of hearing at said first time based on whether the user heard or did not hear sounds at each volume of said plurality of volumes that were produced by said sound generating device at said first time;
   d. using said electronic sound generating device to produce said hearing test audio signal at a second time and determining a second measure of threshold of hearing at said second time based on whether the user heard or did not hear sounds at each volume of said plurality of volumes that were produced by said sound generating device at said second time;

e. comparing said first measure of threshold of hearing at said first time with said second measure of threshold of hearing at said second time; and f. determining that a change in threshold of hearing occurred if said second measure of threshold of hearing differs from said first measure of threshold of hearing.

2. A method as recited in claim 1, wherein said electronic sound generating device comprises a personal listening device.

3. A method as recited in claim 2, wherein said personal listening device includes at least one from the group consisting of an iPod, a Walkman, a CD player, an MP3 player, a DVD player, a video device and a tape player.

4. A method as recited in claim 1, wherein said electronic sound generating device includes a telecommunications device.

5. A method as recited in claim 4, wherein said telecommunications device includes at least one from the group consisting of a phone, a cellular phone, a personal digital assistant, and a walkie talkie.

6. A method as recited in claim 1, wherein said electronic sound generating device comprises a computer.

7. A method as recited in claim 6, wherein said computer includes at least one from the group consisting of a server, a desktop computer, a laptop computer, a notebook computer, a hand held computer, a Palm Pilot, a BlackBerry, and a personal digital assistant.

8. A method as recited in claim 1, wherein said electronic sound generating device includes at least one from the group consisting of a loudspeaker system, head phones, in ear speakers, and over-ear speakers.

9. A method as recited in claim 1, wherein said hearing test audio signal includes sounds at 3 different volume levels.

10. A method as recited in claim 9, wherein said hearing test audio signal includes sounds at 8 different volume levels.

11. A method as recited in claim 1, wherein said hearing test audio signal includes sounds having a predefined decibel difference there between.

12. A method as recited in claim 1, wherein said plurality of volume levels populate a range from below said threshold of hearing of the user to above said threshold of hearing of the user.

13. A method as recited in claim 1, wherein said hearing test audio signal includes sounds separated by silence.

14. A method as recited in claim 1, wherein said hearing test audio signal includes a single sound increasing in decibel level gradually and continually.

15. A method as recited in claim 1, wherein no sound of said hearing test audio signal lasts for more than 5 seconds.

16. A method as recited in claim 1, further comprising an input device and a memory for a user to record data regarding number of tones heard.

17. A method as recited in claim 1, wherein all sounds of said hearing test audio signal are at a single frequency.

18. A method as recited in claim 1, wherein said hearing test audio signal includes sounds at a plurality of frequencies.

19. A method as recited in claim 1, wherein said electronic sound generating device includes a program to automatically play said predefined hearing test audio signal when said device is powered on.

20. A method as recited in claim 1, wherein said electronic sound generating device includes a program to automatically play said predefined hearing test audio signal as said device is powered off.

21. A method as recited in claim 1, wherein said electronic sound generating device includes an input device enabling a user to play said predefined hearing test audio signal when desired.

22. A method as recited in claim 1, wherein said content audio signal includes at least one from the group consisting of a live source, a signal derived from an external source, and a user specified audio signal.

23. A method as recited in claim 1, wherein said content audio signal includes music.

24. A method as recited in claim 1, further comprising after (c) and before (d) exposing the user to sound sufficient to warrant a hearing threshold shift check.

* * * * *